United States Patent
Remmers et al.

(10) Patent No.: US 10,492,722 B2
(45) Date of Patent: Dec. 3, 2019

(54) NON-INVASIVE SYSTEMS AND METHODS FOR IDENTIFYING RESPIRATORY DISTURBANCES EXPERIENCED BY A SUBJECT

(71) Applicant: ZST HOLDINGS, INC., Calgary (CA)

(72) Inventors: John Remmers, Sedona, AZ (US); Zbigniew Ludwik Topor, Calgary (CA); Joshua Grosse, Calgary (CA); Seyed Abdolali Zareian Jahromi, Calgary (CA)

(73) Assignee: ZST Holdings, Inc., Calgary, AB (CA)

( * ) Notice: Subject to any disclaimer, the term of this patent is extended or adjusted under 35 U.S.C. 154(b) by 349 days.

(21) Appl. No.: 15/124,740

(22) PCT Filed: Mar. 10, 2015

(86) PCT No.: PCT/US2015/019739
§ 371 (c)(1),
(2) Date: Sep. 9, 2016

(87) PCT Pub. No.: WO2015/138474
PCT Pub. Date: Sep. 17, 2015

(65) Prior Publication Data
US 2017/0181692 A1    Jun. 29, 2017

Related U.S. Application Data

(60) Provisional application No. 61/950,659, filed on Mar. 10, 2014.

(51) Int. Cl.
*A61B 5/08*    (2006.01)
*A61B 5/00*    (2006.01)

(52) U.S. Cl.
CPC .............. *A61B 5/4818* (2013.01); *A61B 5/08* (2013.01); *A61B 5/0803* (2013.01);
(Continued)

(58) Field of Classification Search
CPC combination set(s) only.
See application file for complete search history.

(56) References Cited

U.S. PATENT DOCUMENTS

| 2,171,695 A | 9/1939 | Harper |
| 4,376,628 A | 3/1983 | Aardse |

(Continued)

FOREIGN PATENT DOCUMENTS

| CN | 1602970 | 4/2005 |
| CN | 101917924 | 12/2010 |

(Continued)

OTHER PUBLICATIONS

International Search Report and Written Opinion of the International Searching Authority dated Jun. 16, 2015 in corresponding PCT App. No. PCT/US2015/019739.

(Continued)

*Primary Examiner* — Eric J Messersmith
(74) *Attorney, Agent, or Firm* — Meunier Carlin & Curfman LLC

(57) ABSTRACT

An example method for detecting respiratory disturbances experienced by a subject can include receiving an airflow signal and at least one of an acoustic or vibration signal, where the airflow, acoustic, and/or vibration signals are associated with the subjects breathing. At least one feature can be extracted from the airflow signal and at least one feature can be extracted from at least one of the acoustic or vibration signal. Based on the extracted features, at least one respiratory disturbance can be detected. The respiratory disturbance can be flow limited breath or inspiratory flow limitation ("IFL").

44 Claims, 12 Drawing Sheets

(52) U.S. Cl.
CPC .......... *A61B 5/0826* (2013.01); *A61B 5/4812* (2013.01); *A61B 5/4815* (2013.01); *A61B 5/682* (2013.01); *A61B 2560/0468* (2013.01)

(56) References Cited

U.S. PATENT DOCUMENTS

| | | | |
|---|---|---|---|
| 4,602,905 A | 7/1986 | O'Keefe | |
| 4,901,737 A | 2/1990 | Toone | |
| 5,030,098 A | 7/1991 | Branford | |
| 5,154,609 A | 10/1992 | George | |
| 5,313,960 A | 5/1994 | Tomasi | |
| 5,365,945 A | 11/1994 | Halstrom | |
| 5,409,017 A | 4/1995 | Lowe | |
| 5,427,117 A | 6/1995 | Thornton | |
| 5,513,986 A | 5/1996 | Feltham et al. | |
| 5,537,994 A | 7/1996 | Thornton | |
| 5,566,683 A | 10/1996 | Thornton | |
| 5,570,704 A | 11/1996 | Buzzard et al. | |
| 5,611,355 A | 3/1997 | Hilsen | |
| 5,642,737 A | 7/1997 | Parks | |
| 5,666,960 A | 9/1997 | Fredberg et al. | |
| 5,671,733 A | 9/1997 | Raviv et al. | |
| 5,678,567 A | 10/1997 | Thornton et al. | |
| 5,755,219 A | 5/1998 | Thornton | |
| 5,782,240 A * | 7/1998 | Raviv ................... | A61B 7/003 600/484 |
| 5,794,627 A | 8/1998 | Frantz et al. | |
| 5,816,799 A | 10/1998 | Parker | |
| 5,823,193 A | 10/1998 | Singer et al. | |
| 5,826,579 A | 10/1998 | Remmers et al. | |
| 5,829,441 A | 11/1998 | Kidd | |
| 5,846,212 A | 12/1998 | Beeuwkes et al. | |
| 5,868,138 A | 2/1999 | Halstrom | |
| 5,884,628 A | 3/1999 | Hilsen | |
| 5,921,942 A | 7/1999 | Remmers et al. | |
| 5,941,247 A | 8/1999 | Keane | |
| 5,953,713 A * | 9/1999 | Behbehani ........... | A61M 16/026 128/204.18 |
| 5,954,048 A | 9/1999 | Thornton | |
| 5,961,447 A | 10/1999 | Raviv et al. | |
| 5,983,892 A | 11/1999 | Thornton | |
| 6,012,920 A | 1/2000 | Woo | |
| 6,041,784 A | 3/2000 | Halstrom | |
| 6,055,986 A | 5/2000 | Meade | |
| 6,109,265 A | 8/2000 | Frantz et al. | |
| 6,155,262 A | 12/2000 | Thornton et al. | |
| 6,161,542 A | 12/2000 | Halstrom | |
| 6,273,859 B1 * | 8/2001 | Remmers ................. | A61F 5/566 600/529 |
| 6,290,654 B1 | 9/2001 | Karakasoglu | |
| 6,305,376 B1 | 10/2001 | Thornton | |
| 6,325,064 B1 | 12/2001 | Thornton | |
| 6,374,824 B1 | 4/2002 | Thornton | |
| 6,450,167 B1 | 9/2002 | David et al. | |
| 6,516,805 B1 | 2/2003 | Thornton | |
| 6,634,353 B1 | 10/2003 | Knebelman et al. | |
| 6,729,335 B1 | 5/2004 | Halstrom | |
| 6,769,910 B1 | 8/2004 | Pantino | |
| 6,877,513 B2 | 4/2005 | Scarberry et al. | |
| 7,146,982 B2 | 12/2006 | Mousselon et al. | |
| 7,174,895 B2 | 2/2007 | Thornton et al. | |
| 7,282,027 B2 | 10/2007 | Sotos et al. | |
| 7,328,698 B2 | 2/2008 | Scarberry et al. | |
| 7,331,349 B2 | 2/2008 | Brady et al. | |
| 7,357,635 B2 | 4/2008 | Belfor et al. | |
| 7,396,333 B2 | 7/2008 | Stahmann et al. | |
| 7,328,705 B2 | 12/2008 | Abramson | |
| 7,637,262 B2 | 12/2009 | Bailey | |
| 7,712,468 B2 | 5/2010 | Hargadon | |
| 7,832,403 B2 | 11/2010 | Halstrom et al. | |
| 7,841,987 B2 | 11/2010 | Sotos et al. | |
| 8,001,973 B2 | 8/2011 | Sotos et al. | |
| 8,025,063 B2 | 9/2011 | Sotos et al. | |
| 8,037,886 B2 | 10/2011 | Sotos et al. | |
| 8,226,407 B2 | 7/2012 | Hanewinkel et al. | |
| 8,550,816 B2 | 10/2013 | Hanewinkel et al. | |
| 8,646,447 B2 | 2/2014 | Martin et al. | |
| 2002/0165462 A1 | 11/2002 | Westbrook et al. | |
| 2003/0224313 A1 | 12/2003 | Bergersen | |
| 2004/0030224 A1 | 2/2004 | Sotos et al. | |
| 2005/0028827 A1 | 2/2005 | Halstrom | |
| 2005/0081859 A1 | 4/2005 | Scarberry et al. | |
| 2005/0175709 A1 | 8/2005 | Baty et al. | |
| 2005/0175954 A1 | 8/2005 | Zacher | |
| 2005/0241646 A1 | 11/2005 | Sotos et al. | |
| 2006/0003292 A1 | 1/2006 | Lauren et al. | |
| 2006/0020178 A1 | 1/2006 | Sotos et al. | |
| 2006/0063981 A1 | 3/2006 | Sotos et al. | |
| 2006/0155205 A1 | 7/2006 | Sotos et al. | |
| 2006/0266356 A1 | 11/2006 | Sotos et al. | |
| 2007/0068534 A1 | 3/2007 | Bailey et al. | |
| 2007/0179395 A1 * | 8/2007 | Sotos ................... | A61B 5/4809 600/529 |
| 2007/0183572 A1 | 8/2007 | Drummond et al. | |
| 2007/0239056 A1 | 10/2007 | Moore | |
| 2007/0283967 A1 | 12/2007 | Bailey | |
| 2007/0283973 A1 | 12/2007 | Longley | |
| 2008/0053461 A1 | 3/2008 | Hirotsuka et al. | |
| 2008/0064008 A1 | 3/2008 | Schmitt | |
| 2008/0076094 A1 | 3/2008 | Hindin | |
| 2008/0236597 A1 | 10/2008 | Bergersen | |
| 2009/0078257 A1 | 3/2009 | Bhat et al. | |
| 2009/0078274 A1 | 3/2009 | Bhat et al. | |
| 2009/0241969 A1 | 10/2009 | Walker | |
| 2010/0018538 A1 | 1/2010 | Sotos et al. | |
| 2010/0101583 A1 | 4/2010 | Chen et al. | |
| 2010/0154802 A1 | 6/2010 | Fuselier | |
| 2010/0163043 A1 | 7/2010 | Hart et al. | |
| 2010/0217426 A1 | 8/2010 | Sotos et al. | |
| 2010/0240982 A1 | 9/2010 | Westbrook et al. | |
| 2010/0300457 A1 | 12/2010 | Horchover | |
| 2010/0316973 A1 | 12/2010 | Remmers et al. | |
| 2011/0005526 A1 | 1/2011 | Garabadian et al. | |
| 2011/0217674 A1 | 9/2011 | Hanewinkel et al. | |
| 2011/0232652 A1 | 9/2011 | Levendowski et al. | |
| 2011/0295083 A1 | 12/2011 | Doelling et al. | |
| 2013/0023797 A1 | 1/2013 | Hanewinkel et al. | |
| 2014/0114146 A1 | 4/2014 | Hanewinkel et al. | |
| 2015/0007830 A1 | 1/2015 | Remmers et al. | |
| 2015/0039045 A1 | 2/2015 | Ni et al. | |
| 2015/0164682 A1 | 6/2015 | Remmers et al. | |
| 2016/0022205 A1 | 1/2016 | Remmers et al. | |

FOREIGN PATENT DOCUMENTS

| | | |
|---|---|---|
| CN | 102481181 | 5/2012 |
| EP | 1832306 | 9/2007 |
| JP | 2001-524852 | 12/2001 |
| WO | 1998/046177 | 10/1998 |
| WO | 2005107590 A1 | 11/2005 |
| WO | 2005/115266 | 12/2005 |
| WO | 2008/151374 | 12/2008 |
| WO | 2010/141868 | 12/2010 |
| WO | 2010/141957 | 12/2010 |
| WO | 2011/082346 | 7/2011 |
| WO | 2011/147985 | 12/2011 |
| WO | 2013/102095 | 7/2013 |
| WO | 2013/188660 | 12/2013 |
| WO | 2014/170855 | 10/2014 |

OTHER PUBLICATIONS

Almeida, F.R., et al., "Effect of a Titration Polysomnogram on Treatment Success with a Mandibular Repositioning Appliance," Journal of Clinical Sleep Medicine, vol. 5, No. 3, 2009, pp. 198-204.

Cartwright, R.D., "Predicting Response to the Tongue Retaining Device for Sleep Apnea Syndrome," Arch. Otolaryngol., vol. 111, 1985, pp. 385-388.

Chan, A.S.L., et al., "Nasopharyngoscopic evaluation of oral appliance therapy for obstructive sleep apnoea," European Respiratory Journal, vol. 35, No. 4, 2010, pp. 836-842.

Clark, S.A., et al., "Assessment of Inspiratory Flow Limitation

(56) References Cited

OTHER PUBLICATIONS

Invasively and Noninvasively during Sleep," American Journal of Respiratory and Critical Care Medicine, vol. 158, 1998, pp. 713-722.
Dort, L.C., et al., "Mandibular advancement and obstructive sleep apnoea: a method for determining effective mandibular protrusion," European Respiratory Journal, vol. 27, No. 5, 2006, pp. 1003-1009.
Friedman, M., et al., "Compliance and Efficacy of Titratable Thermoplastic versus Custom Mandibular Advancement Devices," Otolaryngology-Head and Neck Surgery, vol. 147, No. 2, 2012, pp. 379-386.
Kim, Y.-K., et al., "The influence of the amount of mandibular advancement in the application of mandibular advancement device for obstructive sleep apnea patients," Sleep Medicine and Psychophysiology, vol. 18, No. 6, 2011, pp. 29-34. (English Abstract).
Levendowski, D.J., et al., "Initial Evaluation of a Titration Appliance for Temporary Treatment of Obstructive Sleep Apnea," J. Sleep Disord. Ther., vol. 1, Issue 1, 2011, 8 pages.
Liu, Y., et al., "Cephalometric and physiologic predictors of the efficacy of an adjustable oral appliance for treating obstructive sleep apnea," American Journal of Orthodontics and Dentofacial Orthopedics, vol. 120, No. 6, 2001, pp. 639-647.
Marklund, M., et al., "Treatment Success With a Mandibular Advancement Device Is Related to Supine-Dependent Sleep Apnea," CHEST, vol. 114, No. 6, 1998, pp. 1630-1635.
Morgenstern, C., et al., "Assessment of Changes in Upper Airway Obstruction by Automatic Identification of Inspiratory Flow Limitation During Sleep," IEEE Transactions on Biomedical Engineering, vol. 56, No. 8, 2009, pp. 2006-2015.
Otsuka, R., et al., "A comparison of responders and nonresponders to oral appliance therapy for the treatment of obstructive sleep apnea," American Journal of Orthodontics and Dentofacial Orthopedics, vol. 129, No. 2, 2006, pp. 222-229.
Pételle, B., et al., "One-Night Mandibular Advancement Titration for Obstructive Sleep Apnea Syndrome," American Journal of Respiratory and Critical Care Medicine, vol. 165, 2002, pp. 1150-1153.
Remmers, J., et al., "Remotely Controlled Mandibular Protrusion during Sleep Predicts Therapeutic Success with Oral Appliances in Patients with Obstructive Sleep Apnea," Sleep, vol. 36, No. 10, 2013, pp. 1517-1525A.
Tsai, W.H., et al., "Remotely Controlled Mandibular Positioner Predicts Efficacy of Oral Appliances in Sleep Apnea," American Journal of Respiratory and Critical Care Medicine, vol. 170, No. 4, 2004, pp. 366-370.
Tsuiki, S., et al., "Optimal positive airway pressure predicts oral appliance response to sleep apnoea," European Respiratory Journal, vol. 35, No. 5, 2010, pp. 1098-1105.
Vázquez, J.-C., et al., "Automated analysis of digital oximetry in the diagnosis of obstructive sleep apnoea," Thorax., vol. 55, 2000, pp. 302-307.
De Backer, et al., "Functional imaging using computational fluid dynamics to predict treatment success of mandibular advancement devices in sleep-disordered breathing", Journal of Biomechanics, 2007, vol. 40, pp. 3708-3714.
Kuna et al., "Evaluation of an oral mandibular advancement titration appliance," Oral Surg Oral Med Oral Pathol Oral Radiol Endod, 2006, vol. 101, No. 5, pp. 593-603.

* cited by examiner

200

```
┌─────────────────────────────────────────────────────┐
│ Receive an airflow signal and at least one of an    │
│ acoustic signal or a vibration signal               │
│ 202                                                 │
└─────────────────────────────────────────────────────┘
                          │
                          ▼
┌─────────────────────────────────────────────────────┐
│ Extract at least one feature from the airflow       │
│ signal and at least one feature from at least one   │
│ of the acoustic signal or the vibration signal      │
│ 204                                                 │
└─────────────────────────────────────────────────────┘
                          │
                          ▼
┌─────────────────────────────────────────────────────┐
│ Based on the extracted features, detect at least    │
│ one respiratory disturbance                         │
│ 206                                                 │
└─────────────────────────────────────────────────────┘
```

```
Receive at least one of an acoustic signal or a vibration signal
222
```

↓

```
Extract at least one feature from at least one of the acoustic signal
or the vibration signal
224
```

↓

```
Based on the extracted feature, detect at least one respiratory
disturbance
226
```

*FIG. 2B*

FEATURES OF THE NONINVASIVE CLASSIFIERS

| Index | Description | Index | Description |
|---|---|---|---|
| 1 | Total energy (area) of the PSD | 12 | (area of the first derivative of the inspiration's flow)÷(mean of dV) |
| 2 | Nr. of peaks of dPSD in [0 Hz – PSD0] | 13 | (area of the flow inspiration* from [0s - time of peak amplitude])÷(total area of the inspiration*) |
| 3 | Peak amplitude of the PSD [dB] | 14 | Area of the inspiration* in the interval from [0s – 1/2 of the inspiration's duration] |
| 4 | Energy of the PSD in [0Hz–PSD0] | 15 | (PSD total energy)×(PSD peak amplitude) |
| 5 | PSD0 [Hz] | 16 | (total energy of the PSD) – (energy of the PSD triangle at 20 dB) |
| 6 | Nr. of Peaks of the PSD | 17 | Energy of the PSD triangle at 30 dB |
| 7 | Nr. of peaks in the inspiration's flow shape | 18 | Energy of the PSD in [PSD freq. at 30 dB - end of PSD] |
| 8 | Duration of the inspiration [s] | 19 | Area of the inspiration* from [0s - the first 1/3 of the inspiration] |
| 9 | Amplitude of the inspiration normalized with the patient's peak-flow | 20 | (area of the first 1/3)÷(area of the last 1/3) of the inspiration* |
| 10 | Energy of the PSD in [0.25 – 0.375 Hz] | 21 | (area of the inspiration*) × (inspiration's duration [s]) |
| 11 | Energy of the PSD in [0.375 – 0.5625 Hz] | 22 | Product between the peak frequency of the PSD and the total energy of the PSD | dI*: 1st derivative of the inspiration, dPSD: 1st derivative of the PSD, PSD0: frequency at which the PSD function cross 0 dB, *with amplitude normalization (an inspiration's flow values were divided by the inspiration's maximum flow value).

FIG. 4

NON-INVASIVE SYSTEMS AND METHODS FOR IDENTIFYING RESPIRATORY DISTURBANCES EXPERIENCED BY A SUBJECT

CROSS-REFERENCE TO RELATED APPLICATIONS

This application claims the benefit of U.S. Provisional Patent Application No. 61/950,659, filed on Mar. 10, 2014, entitled "NON-INVASIVE SYSTEMS AND METHODS FOR IDENTIFYING RESPIRATORY DISTURBANCES EXPERIENCED BY A SUBJECT," the disclosure of which is expressly incorporated herein by reference in its entirety.

BACKGROUND

Inspiratory flow limitation ("IFL") is a common component of sleep-disordered breathing. IFL is established by the presence of flow limited breaths. A conventional technique for detecting/identifying IFL breaths, or flow limited breath(s), using supra-glottic pressure and airflow signals has previously been developed. For example, a breath is classified as IFL when there is no increase in airflow associated with a 1 $cmH_2O$ drop in supra-glottic pressure. This is referred to herein as the "gold standard." However, the conventional technique requires catheterization of the subject's pharynx to obtain supra-glottic pressure. Thus, the conventional technique is invasive.

SUMMARY

Systems and methods for detecting respiratory disturbances such as IFL, for example, are described herein. Additionally, systems and methods for detecting respiratory disturbances in the presence of a mandibular displacement device used to treat the respiratory disturbance are described herein. Additionally, systems and methods for performing a titration for oral appliance therapy are described herein. The systems and methods are non-invasive. In other words, the non-invasive systems and methods can detect respiratory disturbances without using supra-glottic pressure, which is measured using a sensor inserted into a subject with a catheter (e.g., a naso-pharyngeal catheter). Conventionally, a breath is classified as IFL when there is no increase in airflow associated with a 1 $cmH_2O$ drop in supra-glottic pressure. Instead, the systems and methods detect respiratory disturbances based on airflow, sound, and/or vibration associated with a subject's breathing.

An example method for detecting respiratory disturbances experienced by a subject can include receiving an airflow signal and at least one of an acoustic signal or a vibration signal, where the airflow, acoustic, and/or vibration signals are associated with the subject's breathing. Optionally, the method can include receiving the airflow signal and both the acoustic and vibration signals. At least one feature can be extracted from the airflow signal and at least one feature can be extracted from at least one of the acoustic signal or the vibration signal. For example, at least one feature can be extracted from each of the airflow signal and at least one of the acoustic signal or the vibration signal, respectively. This disclosure contemplates that the extracted features can be the same feature for each of the airflow signal and at least one of the acoustic signal or the vibration signal. Alternatively, the extracted features can be different features for each of the airflow signal and at least one of the acoustic signal or the vibration signal. Based on the extracted features, at least one respiratory disturbance can be detected.

Another example method for detecting respiratory disturbances experienced by a subject can include receiving at least one of an acoustic signal or a vibration signal, where the acoustic and/or vibration signals are associated with the subject's breathing. Optionally, the method can include receiving both the acoustic and vibration signals. At least one feature can be extracted from at least one of the acoustic signal or the vibration signal. As described above, when a plurality of features are extracted (e.g., at least one feature from each of a plurality of measured signals), the extracted features can be the same or different features for each of the respective signals. Based on the extracted feature, at least one respiratory disturbance can be detected.

Another example method for detecting respiratory disturbances experienced by a subject can include positioning a mandibular displacement device in the subject's oral cavity, and receiving an airflow signal associated with the subject's breathing. At least one feature can be extracted from the airflow signal. Based on the extracted feature, at least one respiratory disturbance can be detected.

An example method for titrating for oral appliance therapy can include positioning an adjustable mandibular displacement device in an oral cavity of a subject during a test period, and titrating a protrusion level of the adjustable mandibular displacement device during the test period in response to detecting at least one respiratory disturbance. The respiratory disturbance can be detected by measuring at least one of an airflow signal, an acoustic signal, or a vibration signal, where the airflow, acoustic and/or vibration signals are associated with the subject's breathing during the test period. Optionally, the method can include measuring both the acoustic and vibration signals. Optionally, the method can include measuring the airflow signal and at least one of the acoustic or vibration signals. Optionally, the method can include measuring the airflow signal and both the acoustic and vibration signals. At least one feature can be extracted from the airflow signal, the acoustic signal, or the vibration signal. As described above, when a plurality of features are extracted (e.g., at least one feature from each of a plurality of measured signals), the extracted features can be the same or different features for each of the respective signals. Based on the extracted feature, at least one respiratory disturbance can be detected.

Alternatively or additionally, the respiratory disturbance can be flow limited breath or IFL. Alternatively or additionally, the method can optionally include diagnosing the subject with high upper airway resistance ("HUAR") (which is also sometimes referred to as upper airway resistance syndrome) based on the detection of the at least one respiratory disturbance. Alternatively or additionally, the method can optionally include assessing oral appliance therapy for the subject diagnosed with flow limited breath, IFL and/or HUAR based on the detection of the at least one respiratory disturbance. For example, the assessment may compare the level of respiratory disturbances during treatment to the level of respiratory disturbance without treatment, or may compare the level of respiratory disturbances during treatment at one setting to the level of respiratory disturbances during treatment at another setting. Optionally, the at least one respiratory disturbance can be detected in real time while the subject is sleeping.

Alternatively or additionally, the respiratory disturbance can be detected using a machine learning module. The machine learning module can be a classifier, a pattern recognition module. Examples of machine learning techniques are neural network, support vector machine, decision tree, AdaBoost. The machine learning module can be trained to classify the subject's breath(s) as respiratory disturbances. For example, the extracted features can be input in the machine learning module, and an output value of the machine learning module can indicate occurrence of at least one respiratory disturbance. Optionally, the machine learning module is a neural network. For example, the neural network can be a feedforward multilayer perceptron neural network. Optionally, the machine learning module can output a numeric signal (e.g., a binary or non-binary, real number output) or non-numeric signal (e.g., IFL or non-IFL). Optionally, the machine learning module can output a binary signal (e.g., 0 or 1). When the output value of the machine learning module is a first value (e.g., 0 or 1), the machine learning module indicates that the respiratory disturbance occurred (e.g., the subject's breath is classified as IFL). When the output value of the machine learning module is a second value (e.g., the other of 1 or 0), the machine learning module indicates that the respiratory disturbance did not occur (e.g., the subject's breath is not classified as IFL). Optionally, the machine learning module can output a non-binary signal. When the output value of the machine learning module is within a first range of values (e.g., a positive value), the machine learning module indicates that the respiratory disturbance occurred (e.g., the subject's breath is classified as IFL). When the output value of the machine learning module is within a second range of values (e.g., a negative value), the machine learning module indicates that the respiratory disturbance did not occur (e.g., the subject's breath is not classified as IFL). Optionally, there can be a range of values (i.e., an indeterminate range or uncertainty category) between or outside of the first and second ranges of values where the machine learning module indicates neither occurrence nor non-occurrence of the respiratory disturbance.

Alternatively or additionally, the features can optionally be extracted from respective portions of the airflow signal, the acoustic signal, and/or the vibration signal corresponding to at least a portion of an inspiration portion of a breath. In other words, the inspiration portion of the breath can be identified in the airflow signal, the acoustic signal, and/or the vibration signal, and the features can be extracted from the respective inspiration portion of the signal(s). Optionally, the features can be extracted from the airflow signal, the acoustic signal, and/or the vibration signal in a time or frequency domain. Alternatively or additionally, the extracted features can include at least one of a shape, magnitude, distribution, duration, or energy of the airflow signal, the acoustic signal, and/or the vibration signal.

Optionally, the extracted features can include a correlation between respective portions of at least two of the airflow, acoustic, and vibration signals. For example, the extracted features can be a correlation (e.g., a cross correlation) between the acoustic and vibration signals. Alternatively or additionally, the extracted features can include a correlation between respective extracted features of at least two of the airflow, acoustic, and vibration signals.

Optionally, the extracted features can include a sound formant. Alternatively or additionally, the extracted features can include a feature related to a power spectral density of the airflow signal, the acoustic signal, or the vibration signal. Alternatively or additionally, the extracted features can include a feature related to a short time frequency analysis of the airflow signal, the acoustic signal, or the vibration signal. Alternatively or additionally, the extracted features can include a correlation between at least two of the airflow signal, the acoustic signal, and the vibration signal. Alternatively or additionally, the extracted features can include a correlation between time or frequency analyses of at least two of the airflow signal, the acoustic signal, and the vibration signal.

Optionally, the extracted features can include a plurality of values of the airflow signal, the acoustic signal, or the vibration signal in the frequency domain. Each respective value can be a total energy of the airflow signal, the acoustic signal, or the vibration signal over a predetermined frequency span. The predetermined frequency span can optionally be between 30 and 50 Hz, e.g., 40 Hz. For example, when the predetermined frequency span is 40 Hz, the airflow signal, the acoustic signal, or the vibration signal can be integrated over 40 Hz increments (e.g., 0-39 Hz, 40-79 Hz, 80-119 Hz, etc.) to obtain the total energy for each respective predetermined frequency span.

Alternatively or additionally, the method can optionally include normalizing the airflow signal, the acoustic signal, and/or the vibration signal. Alternatively or additionally, the method can include filtering the airflow signal, the acoustic signal, and/or the vibration signal. The filter can optionally be a smoothing, low-pass, band-pass, or high-pass filter. This disclosure contemplates using analog and/or digital filtering techniques.

Alternatively or additionally, the airflow signal can be based on the air pressure measured in the subject's nostrils. Optionally, the airflow signal can be based on air pressure measured separately in each of the subject's nares. Alternatively or additionally, the airflow signal can be enhanced by the presence of the mandibular displacement device, for example, by the reduction of the airflow though the oral cavity.

Alternatively or additionally, the acoustic signal or the vibration signal can be measured using a sensor mounted on a mandibular displacement device. Optionally, each of the acoustic signal or the vibration signal can be measured using a plurality of sensors (e.g., two sensors such as microphones for measuring the acoustic signal). Alternatively or additionally, the sensor is optionally positioned in the subject's oral cavity. The sensor positioned in the subject's oral cavity can be mounted on the mandibular displacement device or can be mounted directly on a surface of the subject's oral cavity (e.g., teeth, gums, palate). Optionally, the sensor can be placed in the subject's oral cavity but not mounted on the mandibular displacement device. Optionally, the sensor can be mounted on the mandibular displacement device outside of the subject's oral cavity. Alternatively or additionally, the sensor can optionally be a plurality of sensors.

The sensor can optionally be a transducer (e.g., a microphone), accelerometer, or strain gauge configured to measure the acoustic signal. Alternatively or additionally, the sensor can optionally be an accelerometer or strain gauge configured to measure vibration signal. Optionally, the mandibular displacement device can be arranged in the subject's oral cavity. In addition, the mandibular displacement device can reduce airflow through the subject's oral cavity. Alternatively or additionally, the mandibular displacement device can be firmly attached to the subject's teeth.

A system for detecting respiratory disturbances experienced by a subject can include a mandibular displacement device, a sensor for measuring an airflow signal, an acoustic signal, or a vibration signal associated with the subject's breathing, and a processor and memory operatively coupled to the processor. The sensor can be arranged in proximity to the subject's oral or nasal cavity. Optionally, the sensor can be mounted on a mandibular displacement device. The memory can have computer-executable instructions stored thereon that, when executed by the processor, cause the processor to receive the airflow signal, the acoustic signal, or the vibration signal, extract at least one feature from the airflow signal, the acoustic signal, or the vibration signal, and detect, based on the extracted feature, at least one respiratory disturbance.

Optionally, the system can have a plurality of sensors, e.g., for measuring both the acoustic and vibration signals associated with the subject's breathing. The memory can have further computer-readable instructions stored thereon that, when executed by the processor, cause the processor to extract a plurality of features from the acoustic signal and the vibration signal. Optionally, the sensor can be a transducer (e.g., a microphone), accelerometer, or strain gauge configured to measure the acoustic signal. Optionally, the sensor can be an accelerometer or strain gauge configured to measure the vibration signal. As described above, when a plurality of features are extracted (e.g., at least one feature from each of a plurality of measured signals), the extracted features can be the same or different features for each of the respective signals.

Optionally, the system can have a plurality of sensors, e.g., for measuring the airflow signal and at least one of the acoustic signal or the vibration signal. The airflow signal can be based on the air pressure measured in the subject's nostrils. Optionally, the airflow sensor can be configured to measure air pressure separately in each of the subject's nares. The memory can have further computer-executable instructions stored thereon that, when executed by the processor, cause the processor to receive the airflow signal and extract a plurality of features from the airflow signal and at least one of the acoustic signal or the vibration signal. Optionally, the features can be extracted from the airflow signal and both the acoustic and vibration signals. As described above, when a plurality of features are extracted (e.g., at least one feature from each of a plurality of measured signals), the extracted features can be the same or different features for each of the respective signals.

Alternatively or additionally, the sensor can be mounted to a mandibular displacement device. For example, the mandibular displacement device can be an oral appliance, and the sensor can be mounted to a portion of the oral appliance (e.g., upper and/or lower dental trays, upper and/or lower brackets). Alternatively or additionally, the mandibular displacement device can include a motor for controlling protrusion level of the oral appliance, and the sensor can be mounted on a housing for the motor. For example, a microphone, accelerometer or strain gauge can be mounted or fixed to a housing of the mandibular displacement device. Alternatively or additionally, an accelerometer or strain gauge can be mounted or fixed to a housing or bracket of the mandibular displacement device. Alternatively or additionally, the microphone, accelerometer or strain gauge can be mounted or fixed to the mandibular displacement device such that it is arranged in the subject's oral cavity. Alternatively or additionally, the microphone, accelerometer or strain gauge can be arranged in the subject's oral cavity and not mounted on the mandibular displacement device.

Optionally, the mandibular displacement device is any device that protrudes the mandible relative to the maxilla. Alternatively or additionally, the mandibular displacement device, or a portion thereof, can be arranged in the subject's oral cavity. The portion in the subject's oral cavity may be an appliance (e.g., the oral appliance or dental appliance). The appliance may consist of at least an upper or lower dental tray. The dental tray may be fixed rigidly to the teeth by the use of impression material or thermal setting material. Optionally the mandibular displacement device is a device that can move the mandible automatically, remotely, or manually. Optionally, mandibular displacement device may be an oral appliance. Optionally or alternatively, the mandibular displacement device may be the oral appliance that the subject wears for treatment, a temporary appliance that is provided for the purpose of a test or in advance of a custom fabricated oral appliance. The oral appliance may be adjustable or may be fixed at a set protrusive position. Optionally, the mandibular displacement device can reduce airflow through the subject's oral cavity. Optionally, a portion of the mandibular displacement device can be firmly attached to the subject's teeth.

Alternatively or additionally, the system can include machine learning module. The machine learning module can be a classifier, a pattern recognition module, or a neural network, for example. Examples of machine learning techniques are neural network, support vector machine, decision tree, AdaBoost. The machine learning module can be trained to classify the subject's breath(s) as respiratory disturbances. For example, the extracted features can be input in the machine learning module, and an output value of the machine learning module can indicate occurrence of the at least one respiratory disturbance. Optionally, the machine learning module can be a neural network. For example, the neural network can be a feedforward multilayer perceptron neural network. Optionally, the machine learning module can output a numeric signal (e.g., a binary or non-binary, real number output) or non-numeric signal (e.g., IFL or non-IFL). Optionally, the machine learning module can output a binary signal (e.g., 0 or 1). When the output value of the machine learning module is a first value (e.g., 0 or 1), the machine learning module indicates that the respiratory disturbance occurred (e.g., the subject's breath is classified as IFL). When the output value of the machine learning module is a second value (e.g., the other of 1 or 0), the machine learning module indicates that the respiratory disturbance did not occur (e.g., the subject's breath is not classified as IFL). Optionally, the machine learning module can output a non-binary signal. When the output value of the machine learning module is within a first range of values (e.g., a positive value), the machine learning module indicates that the respiratory disturbance occurred (e.g., the subject's breath is classified as IFL). When the output value of the machine learning module is within a second range of values (e.g., a negative value), the machine learning module indicates that the respiratory disturbance did not occur (e.g., the subject's breath is not classified as IFL). Optionally, there can be a range of values (i.e., an indeterminate range or uncertainty category) between or outside of the first and second ranges of values where the machine learning module indicates neither occurrence nor non-occurrence of the respiratory disturbance.

It should be understood that the system can be configured to detect respiratory disturbances and/or perform a titration according to the methods described above.

It should be understood that the above-described subject matter may also be implemented as an article of manufacture, such as a non-transitory computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 2A is a flow diagram illustrating example operations for detecting respiratory disturbances using airflow (e.g., the airflow signal) and at least one of sound (e.g., the acoustic signal) or vibration (e.g., the vibration signal). FIG. 2B is a flow diagram illustrating example operations for detecting respiratory disturbances using at least one of sound or vibration.

FIG. 4 is a chart showing example non-invasive features that can be extracted from the airflow signal.

DETAILED DESCRIPTION

Figure 1:
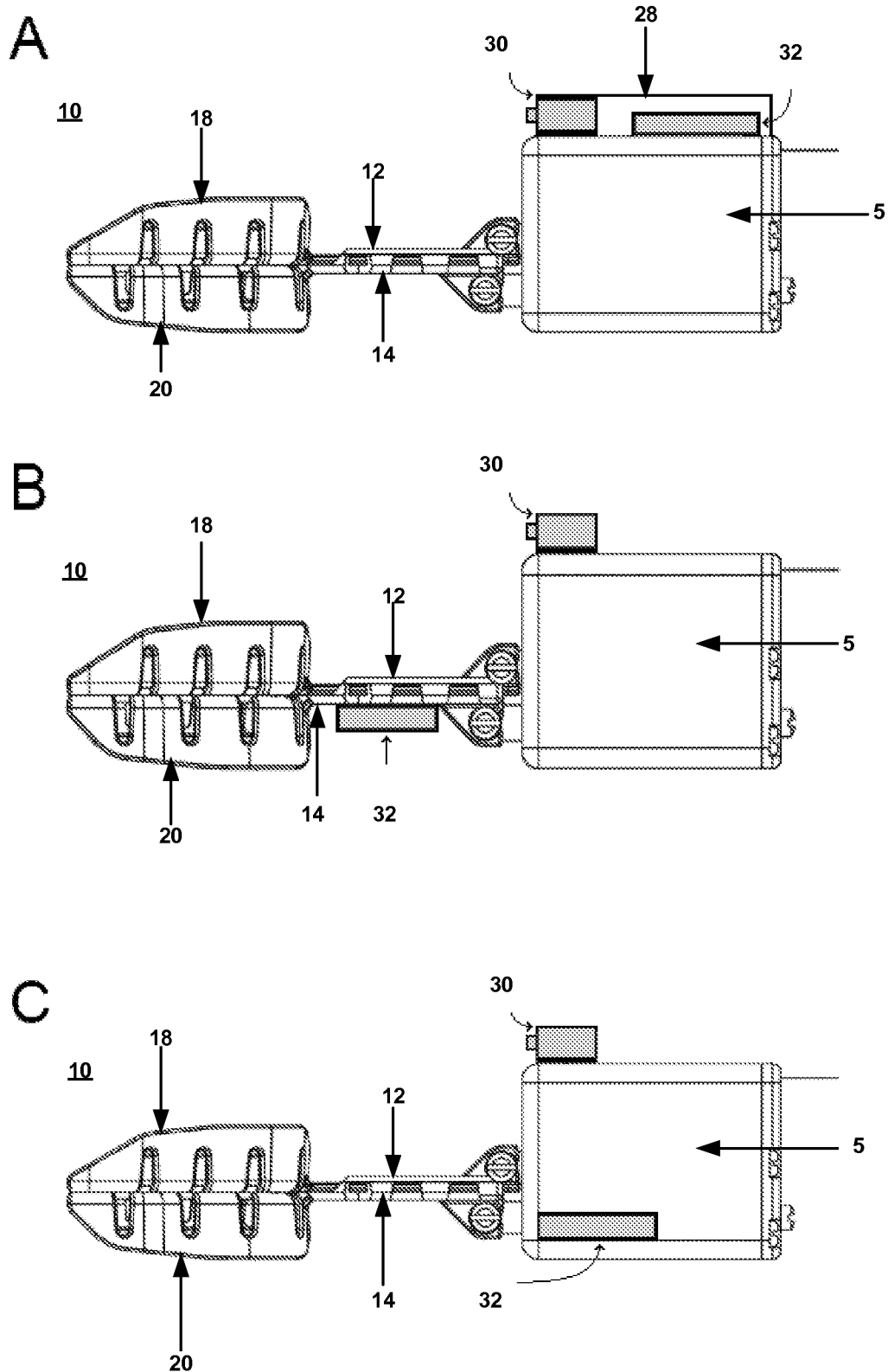
FIGS. 1A-1C are block diagrams of example mandibular displacement devices as described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for identifying respiratory disturbances experienced by a subject that is sleeping with an oral appliance in place and/or performing titration for oral appliance therapy, it will become evident to those skilled in the art that the implementations are not limited thereto.

Non-invasive methods and systems for identifying respiratory disturbances (e.g., flow limited breath or inspiratory flow limitation) experienced by a subject that is sleeping are described herein. Non-invasive methods and systems for identifying respiratory disturbances (e.g., flow limited breath or inspiratory flow limitation) experienced by a subject that is sleeping with mandibular displacement device and/or oral appliance in place are described herein. For example, non-invasive techniques for accurately identifying IFL of a subject, for the purpose of diagnosis, titration or assessment, are described herein. For example, non-invasive techniques for accurately identifying IFL when an oral appliance ("OA") is in the oral cavity (e.g., the mouth) of a subject are described herein.

As used herein, a mandibular displacement device is any device that protrudes the subject's mandible relative to the subject's maxilla. The mandibular displacement device, or a portion thereof, can be arranged in the subject's oral cavity. Optionally, the mandibular displacement device can reduce airflow through the subject's oral cavity. Optionally, a portion of the mandibular displacement device can be firmly attached to the subject's teeth. For example, the mandibular displacement device can be an oral appliance. Optionally, the mandibular displacement device can be the oral appliance that the subject wears for treatment, a temporary oral appliance provided for the purpose of a test or in advance of a custom-fabricated oral appliance. The oral appliance can be adjustable or may be fixed at a set protrusive position. This disclosure contemplates that the mandibular displacement device can be any known oral appliance (or dental appliance). For example, example oral appliances include SOMNODENT of SOMNOMED LTD. of SYDNEY, AUSTRALIA and NARVAL CC of RESMED of SAN DIEGO, Calif. Additionally, WO2013-102095, entitled "Oral appliances and methods of use" describes example oral appliances. The oral appliance can include at least an upper or lower dental tray. The dental tray can optionally be fixed rigidly to the teeth by the use of impression material or thermal setting material. Optionally, the mandibular displacement device can be configured to move the subject's mandible automatically, remotely, or manually. For example, the mandibular displacement device can include the oral appliance, as well as a mechanism for adjusting the protrusion level of the oral appliance. The oral appliance can be configured for manual adjustment, for example, using a screw. Alternatively, the oral appliance can be configured for automatic or remote adjustment using a motor. U.S. Pat. No. 5,826,579 describes an example remote-controlled mandibular displacement device.

Referring now to FIGS. 1A-1C, an example mandibular displacement device 10 according to implementations described herein is shown. It should be understood that the techniques described herein should not be limited to use with the example mandibular displacement device shown in FIGS. 1A-1C. This disclosure contemplates that any mandibular displacement device can be used with the techniques described herein. Optionally, at least a portion of the mandibular displacement device 10 can be arranged in the subject's oral cavity. In addition, the mandibular displacement device 10 can reduce airflow through the subject's oral cavity. The reduction in airflow may affect the quality, characteristics and/or detection of one or more of the signals (e.g., the airflow, acoustic, and/or vibration signal). For example, the presence of a mandibular displacement device in the oral cavity can affect the vibration resulting from a flow limited breath or IFL. Alternatively or additionally, the mandibular displacement device can increase the airflow through the nares as a result of preventing leak through the oral cavity. Alternatively or additionally, the mandibular displacement device can alter the acoustic sound from the respiratory disturbance or the detection of the sound outside of the oral cavity. Alternatively or additionally, the mandibular displacement device 10 can be firmly attached to the subject's teeth. The method and characteristics of the attachment may further affect the signal, the extracted features and therefore the detected respiratory disturbance (e.g., the vibration may be dampened or enhanced by the attachment). The mandibular displacement device 10 is an example of the "adjustable mandibular displacement device" or the "oral device" described below. Remotely controlled mandibular displacement devices are known in the art. For example, U.S. Pat. No. 5,826,579 describes a remotely-controlled mandibular repositioner that is controlled by a technician, and U.S. Pat. No. 6,273,859 describes a remotely-controlled mandibular repositioner that is adaptively controlled by a computer. Although implementations are described herein with regard to the mandibular displacement device 10 shown in FIGS. 1A-1C, it should be understood that other oral appliances (or dental appliances) are contemplated. For example, an oral device may be any device that has capability to reposition the mandible.

As shown in FIGS. 1A-1C, the mandibular displacement device 10 includes an upper tray 18 and a lower tray 20. Additionally, a sensor such as a transducer (e.g., a microphone) for detecting acoustic energy 30 (e.g., the acoustic signal) generated by the subject can be arranged in proximity to at least one of the upper tray 18 and the lower tray 20. This disclosure contemplates that the sensor for detecting the acoustic signal can alternatively be an accelerometer or strain gauge. The accelerometer or strain gauge may be placed directly on the subject, for example, on the subject's throat close to the source of the flow limitation. Alternatively or additionally, a sensor such as an accelerometer for detecting vibrational energy 32 (e.g., the vibration signal) can be arranged in proximity to at least one of the upper tray 18 and the lower tray 20. This disclosure contemplates that the sensor for detecting the vibration signal can alternatively be a strain gauge. The sensor (e.g., sensors 30 and/or 32) can optionally be mounted on or fixed to the mandibular displacement device 10 as shown in FIGS. 1A-1C. The sensor (e.g., sensors 30 and/or 32) can optionally be arranged in any manner relative to the mandibular displacement device 10 such that the sensor can detect acoustic and/or vibrational energy. As shown in FIG. 1A, the sensor (e.g., sensors 30 and 32) is provided in a sensor housing 28, which is mounted on or fixed to a housing 5 of the mandibular displacement device 10. The sensor housing 28, or the sensors (e.g., sensors 30 and 32) can be removable or may be permanently fixed to the mandibular displacement device 10. As shown in FIG. 1B, sensor 30 (e.g., a microphone) is mounted on or fixed to a housing 5 of the mandibular displacement device 10, and sensor 32 (e.g., an accelerometer or strain gauge) is mounted on or fixed to a bracket (e.g., upper or lower bracket 12, 14) of the mandibular displacement device 10. As shown in FIG. 1C, sensor 30 (e.g., a microphone) is mounted on or fixed to a housing 5 of the mandibular displacement device 10, and sensor 32 (e.g., an accelerometer or strain gauge) is embedded within a housing 5 of the mandibular displacement device 10. The placement of the sensor can be chosen to most sensitively measure the designated signal (e.g., the airflow, acoustic, and/or vibration signal). For example, sensor 32 may more accurately measure vibration if attached directly to the component that is fixed rigidly to the subject's dentition. Alternatively or additionally, for example, the sensor 30 may be placed in front of the subject's oral or nasal cavity, directed at the source of the acoustic signal. Fixing the sensor at a known and fixed proximity can increase the detection accuracy.

This disclosure contemplates that the sensors (e.g., sensors 30 and/or 32) can be mounted on or fixed to the mandibular displacement device 10 in positions or arrangements other than those illustrated in FIGS. 1A-1C, which are provided only as examples. For example, the sensor is optionally positioned in the subject's oral cavity. The sensor positioned in the subject's oral cavity can be mounted on the mandibular displacement device, for example, on the oral appliance (e.g., on a portion of a dental tray and/or bracket). Alternatively or additionally, the sensor can be arranged in the oral cavity without mounting on the mandibular displacement device. For example, the sensor can be mounted directly on a surface of the subject's oral cavity (e.g., teeth, gums, palate). Optionally, the sensor can be placed in the subject's oral cavity but not mounted on the mandibular displacement device. Further, although FIGS. 1A-1C illustrate both sensors (e.g., sensors 30 and 32), it should be understood that this disclosure contemplates providing either sensor (e.g., sensor 30 or 32) or both sensors (e.g., sensors 30 and 32) in the methods and systems described below. For example, sensor 30 or 32 can be mounted or fixed on the mandibular displacement device 10 such that the sensor is arranged in the subject's oral cavity during sleep (e.g., mounted on or fixed to at least one of the upper or lower trays 18, 20).

The upper and lower trays 18 and 20 are attachable to an upper bracket 12 and a lower bracket 14, respectively. Additionally, the mandibular displacement device 10 can optionally include a motor and linear actuator such as a brushless DC motor and linear actuator, which are provided in a housing 5. The specifications of the motor and linear actuator can be selected to limit a maximum travel distance (e.g., to provide a maximum of 12 mm of mandibular protrusion) and/or a maximum amount of force applied to a subject's teeth (e.g., 2.5 kg-force), for example. The motor and linear actuator are configured to precisely adjust the relative position of the upper and lower brackets 12 and 14. In addition, the upper and lower trays 18 and 20 can be manually or mechanically adjusted to closely approximate a fully-retruded position of a subject's mandible. The fully-retruded position can be determined by investigation during a clinical visit. Thus, the linear actuator can be set at the fully withdrawn position when the mandible is fully-retruded. By actuating the DC motor and linear actuator, it is possible to adjust the relative position of the upper and lower brackets 12 and 14, and therefore, the relative position of the upper and lower trays 18 and 20. This exerts a force on a subject's lower jaw (mandible) to either protrude or retrude it relative to the subject's upper jaw (maxilla).

Alternatively, the mandibular displacement device 10 can include only an upper and a lower tray that is fit to the patient's teeth, where the trays are held in a position relative to each other by a fixed means. For example by use of a clasp, hook, fin or other mechanism of protruding the subject's mandible relative to the maxilla. The mechanism allows for the upper and lower tray to be adjusted relative to each other. Alternatively, adjusting protrusion of the subject's mandible can require changing to a new upper or lower tray. In other words, a plurality of dental appliances, each having a fixed protrusion level, can be used.

The upper and lower trays 18 and 20 can be fabricated for the subject's upper and lower teeth. This allows a close fitting of the upper and lower trays 18 and 20 to the subject's teeth so that a minimum amount of material occupies the inner surface of the teeth, which minimizes encroachment on the lingual space. This facilitates obtaining a high predictive accuracy of the titration or the assessment because encroachment on the lingual space modifies the tongue position so that the oral mechanics during the titration or assessment do not mimic that which occurs when the therapeutic, custom-fitted oral appliance is used.

A system for detecting respiratory disturbances experienced by a subject can include a mandibular displacement device. For example, the mandibular displacement device of FIGS. 1A-1C. Alternatively or additionally, the mandibular displacement device can be any oral appliance. Optionally, the oral appliance can be adjustable, e.g., a protrusion level of the oral appliance is adjustable. Additionally, the system can include at least one sensor arranged in proximity to the mandibular displacement device. The sensor(s) can be configured to measure at least one of an airflow signal, an acoustic signal, or a vibration signal associated with the subject's breathing. The system can be used to detect respiratory disturbances based on any of the techniques described herein, for example: (i) using at least one of the airflow signal, the acoustic signal, or the vibration signal, (ii) using both the acoustic signal and the vibration signal, (iii) using the airflow signal and at least one of the acoustic signal or the vibration signal, or (iv) using the airflow signal, the acoustic signal, and the vibration signal. Optionally, the system can be used to perform a titration or assessment for oral appliance therapy.

The system can optionally include a sensor configured to measure the airflow signal. Optionally, the airflow signal can be based on air pressure measured separately in each of the subject's nostrils (or nares). An example technique for measuring airflow from air pressure in each nostril is described in WO2014-159236, entitled "SYSTEMS AND METHODS FOR PROVIDING AN AUTOMATED TITRATION FOR ORAL APPLIANCE THERAPY", which is incorporated herein by reference in its entirety. For example, two channels can be used to measure the airflow in the subject's right and left nostrils. For each channel, a MEASUREMENT SPECIALTIES MS4515 pressure transducer from TE CONNECTIVITY LTD. of HAMPTON, Va. can be used. The pressure signals from each channel can optionally be sampled at 350 Hz. The baseline value for each channel can be calculated as a median of the pressure signal within the last predetermined period (e.g., a 20 minute period), for example. The total airflow can be calculated as the resultant of airflow in each of the subject's nostrils, which is the square root of output minus the baseline value. This technique for measuring airflow delivers a qualitative flow shape. Additionally, one or more breaths (including inspiration portions thereof) can be detected or identified in the airflow signal. For example, an inspiration portion of each breath can be detected or identified by the zero-line crossing of airflow signal. Optionally, it is proven that the total airflow signal and a simultaneous pneumotachographic flow signal are comparable in both shape and amplitude if a quadratic root conversation is performed. It should be understood that the techniques for measuring the airflow signal described above (including the specific pressure transducer, sampling frequency, processing steps, etc.) are provided only as examples and that other techniques for measuring the airflow signal can be used.

Alternatively or additionally, the system can optionally include a sensor configured to measure the acoustic signal (e.g., a transducer such as a microphone). For example, the sensor for measuring the acoustic signal can be sensor 30 of FIGS. 1A-1C. The sensor can optionally measure the sound emanating from the subject while snoring. The sensor for measuring the acoustic signal can be arranged as described above with regard to FIGS. 1A-1C. In these examples, the sensor for measuring the acoustic signal is fixed in relation to the subject's face. The sensor for measuring the acoustic signal can optionally be an omnidirectional electret condenser microphone, WM-61A, of PANASONIC CORP. of KADOMA, OSAKA, JAPAN. The acoustic signal can optionally be conditioned and digitized at 22,050 Hz using a data acquisition card ("DAQ") such as NI 9234 and NI cDAQ-9172, NATIONAL INSTRUMENTS CORP. of AUSTIN, Tex. It should be understood that the techniques for measuring the acoustic signal described above (including the specific transducer, sampling frequency, processing steps, etc.) are provided only as examples and that other techniques for measuring the acoustic signal can be used.

Alternatively or additionally, the system can optionally include a sensor configured to measure the vibration signal (e.g., an accelerometer or strain gauge). For example, the sensor for measuring the vibration signal can be sensor 32 of FIGS. 1A-1C. The sensor can optionally measure vibration in the anterior-posterior direction. The sensor for measuring the vibration signal can be arranged as described above with regard to FIGS. 1A-1C. In these examples, the sensor for measuring the vibration signal is fixed in relation to the subject's face or the source of the signal. In these examples, the sensor for measuring vibration signal can optionally be fixed to the component that can most accurately and sensitively detects the vibration signal, for example as attached to the bracket of the dental tray that is firmly attached to the subject's teeth. The sensor for measuring the vibration signal can optionally be a unidirectional accelerometer such as a DELTATRON ACCELEROMETER Type 4508 from Brüel & Kjaer of NAERUM, DENMARK. The vibration signal can optionally be conditioned and digitized at 2,560 Hz using a DAQ such as NI 9234 and NI cDAQ-9172, NATIONAL INSTRUMENTS CORP. of AUSTIN, Tex. It should be understood that the techniques for measuring the vibration signal described above (including the specific accelerometer, sampling frequency, processing steps, etc.) are provided only as examples and that other techniques for measuring the vibration signal can be used.

Figure 3:
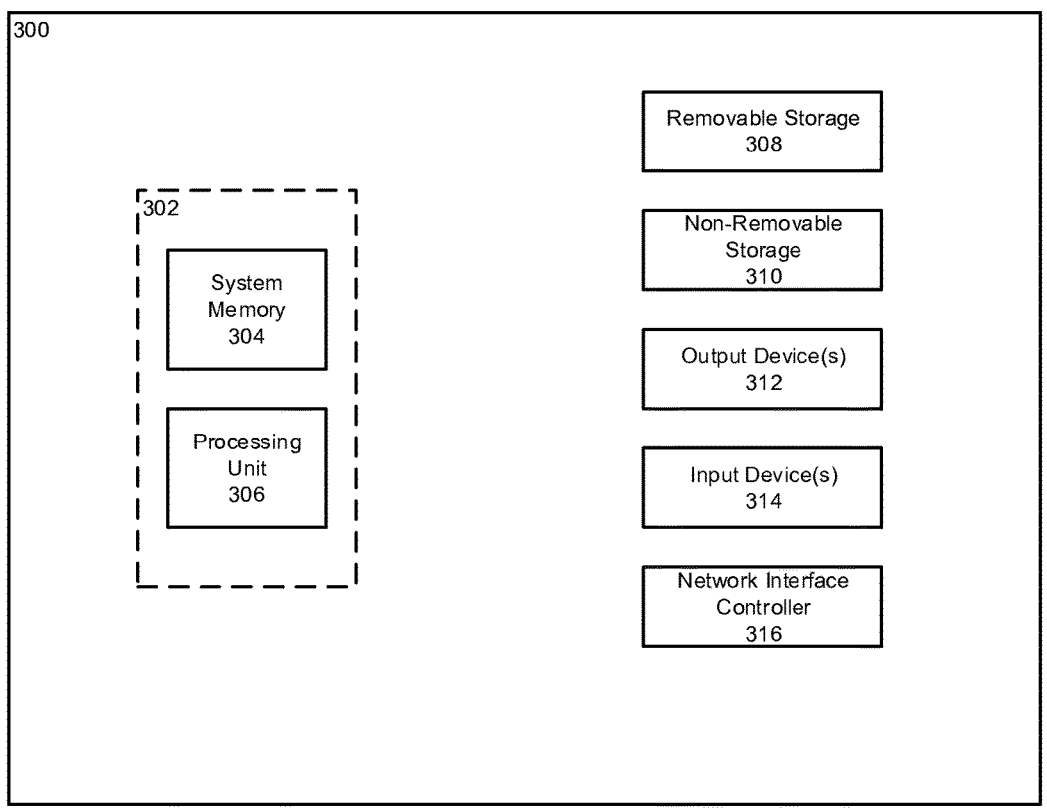
FIG. 3 is an example computing device.
Figure 5A:
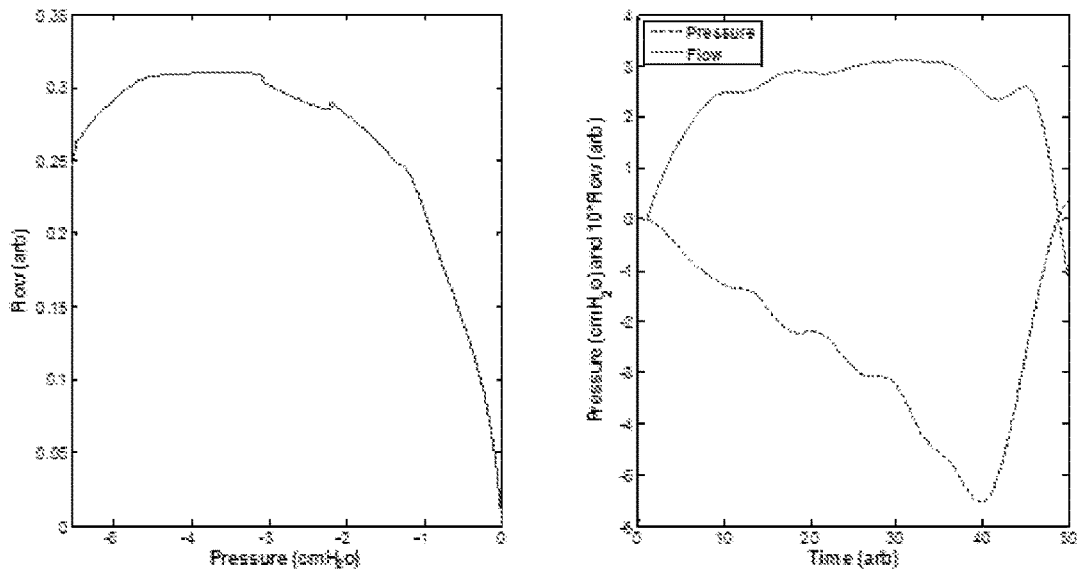
FIGS. 5A-5B are graphs illustrating example IFL breaths (FIG. 5A) and non-IFL breaths (FIG. 5B).
Figure 5B:
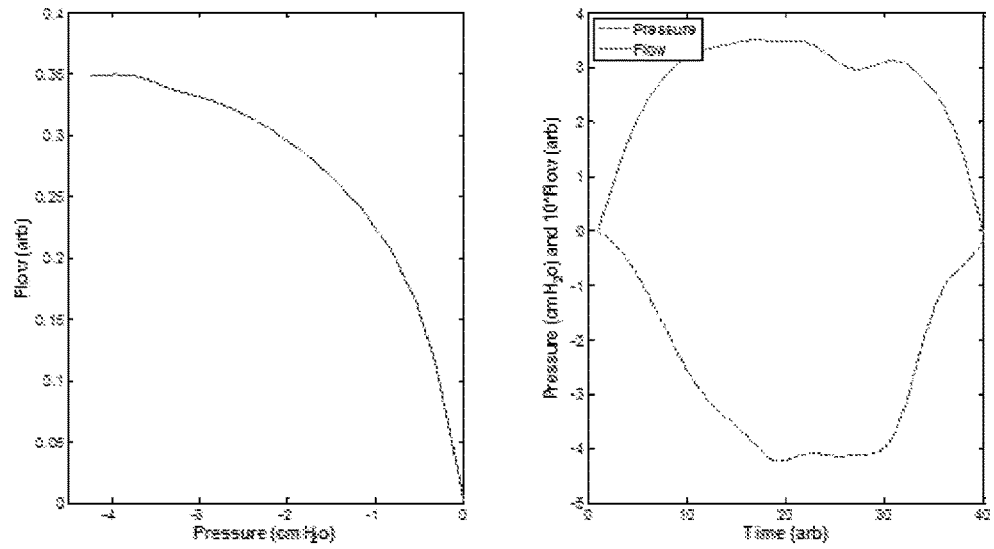

The system can also include a processor and a memory operatively coupled to the processor (e.g., the computer device of FIG. 3). The memory can have computer-executable instructions stored thereon that, when executed by the processor, cause the processor to: receive the airflow signal, the acoustic signal, or the vibration signal; extract at least one feature from the airflow signal, the acoustic signal, or the vibration signal; and detect, based on the extracted feature, at least one respiratory disturbance. This disclosure contemplates that feature extraction and/or respiratory disturbance detection can be performed in real-time while the subject is sleeping or offline. Additionally, this disclosure contemplates that feature extraction and/or respiratory disturbance detection can be performed by more than one computing device. The respiratory disturbance can be flow limited breath or inspiratory flow limitation (IFL).

Optionally, the system can have a plurality of sensors, e.g., for measuring both the acoustic and vibration signals associated with the subject's breathing. In this implementation, the memory can have further computer-readable instructions stored thereon that, when executed by the processor, cause the processor to extract a plurality of features from the acoustic signal and the vibration signal. As described above, when a plurality of features are extracted (e.g., at least one feature from each of a plurality of measured signals), the extracted features can be the same or different features for each of the respective signals.

Optionally, the system can have a plurality of sensors, e.g., for measuring the airflow signal and at least one of the acoustic signal or the vibration signal. In this implementation, the memory can have further computer-executable instructions stored thereon that, when executed by the processor, cause the processor to receive the airflow signal and extract a plurality of features from the airflow signal and at least one of the acoustic signal or the vibration signal. Optionally, the features can be extracted from the airflow signal and both the acoustic and vibration signals. As described above, when a plurality of features are extracted (e.g., at least one feature from each of a plurality of measured signals), the extracted features can be the same or different features for each of the respective signals.

Alternatively or additionally, the system can optionally include machine learning module. The machine learning module can be a classifier, a pattern recognition module. Examples of machine learning techniques are neural network, support vector machine, decision tree, AdaBoost. The machine learning module can be trained to classify the subject's breath(s) as respiratory disturbances. For example, the extracted features can be input in the machine learning module, and an output value of the machine learning module can indicate occurrence of the respiratory disturbance. Optionally, the machine learning module can be trained using features extracted from breaths collected while the subject slept with a mandibular displacement device positioned in the oral cavity. Optionally, the machine learning module can be a neural network such as a feedforward multilayer perceptron neural network.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

An example method for detecting respiratory disturbances experienced by a subject can include measuring at least one of acoustic energy (e.g., the acoustic signal), vibrational energy (e.g., the vibration signal) and airflow (e.g., the airflow signal) generated by the subject and detecting at least one respiratory disturbance based on the at least one of the measured acoustic energy, the vibrational energy and the airflow generated by the subject. The respiratory disturbance can be flow limited breath or IFL.

The detection can be made using a classifier, a pattern recognition system, or a machine learning system. For example, the detection can be made using a neural network trained using features of the at least one of the measure acoustic signal, vibrational signal and airflow as inputs. Alternatively or additionally, the detection can be made using a neural network trained using features that were extracted from breaths collected when the subject slept with a mandibular displacement device in the oral cavity. The features can include at least one of shape, frequency or time domain extracted from a portion of a breath. The portion of the breath can be an inspiration portion, for example.

As described above, the acoustic signal can be detected using a microphone, for example, a microphone for detecting acoustic signal generated by the subject that is arranged in proximity to at least one of the upper tray and the lower tray of a mandibular displacement device. The microphone can be arranged in the subject's oral cavity. Alternatively, the microphone can be arranged external to the subject's oral cavity. Alternatively or additionally, the acoustic signal can be detected by an accelerometer or strain gauge. As described above, the vibrational signal can be measured using an accelerometer or strain gauge.

Optionally, the method can further include positioning a device in the mouth of the subject. The device can be a mandibular displacement device (e.g., the mandibular displacement device 10 shown in FIGS. 1A-1C). Alternatively, the mandibular displacement device may be an oral appliance, such as an oral appliance that would be used to treat flow limited breath, IFL, high upper airway resistance or other sleep disordered breathing (e.g. obstructive sleep apnea). The device can reduce airflow through the subject's oral cavity. The reduction in airflow can affect the signals (e.g., the airflow, sound, and/or vibration signals). The extracted features can be features that were determined based on data collected while the subject had an oral appliance positioned in the subject's oral cavity. Having an oral appliance in the oral cavity changes the physics in the pharynx and thus can affect directly the acoustic or vibration signal. For example, the breaths were collected from subjects sleeping with a mandibular displacement device in the oral cavity and the breaths were used to train the neural network. The extracted features can therefore be used to detect flow limited breath and/or IFL respiratory disturbances when the subject is sleeping with a mandibular displacement device in the mouth. Additionally, the device can be firmly attached to the subject's teeth. Additionally, at least one of the sound and vibration sensors can be attached to the device.

Optionally, the method can further include diagnosing the subject with HUAR based on the correlation. Optionally, the method can further include assessing the treatment of HUAR for the subject based on the correlation.

An example method for titrating for oral appliance therapy can include positioning an adjustable mandibular displacement device in an oral cavity of a subject during a test period. The adjustable mandibular displacement device can be the mandibular displacement device 10 shown in FIGS. 1A-1C. The method can further include measuring at least one of acoustic, vibration, or airflow signal generated by the subject during the test period, detecting at least one respiratory disturbance based on the measured acoustic, the vibrational, or the airflow signal generated by the subject, and titrating a protrusion level of the adjustable mandibular displacement device during the test period in response to detecting the at least one respiratory disturbance.

The detection can be made using a classifier, a pattern recognition system, or a machine learning system. For example, the detection can be made using a neural network trained using features of the at least one of the measure acoustic energy, vibrational energy and airflow as inputs. The features can include at least one of shape, frequency or time extracted from a portion of a breath. The portion of the breath can be an inspiration portion, for example.

Referring now to FIG. 2A, a flow diagram illustrating example operations 200 for detecting respiratory disturbances using airflow and at least one of sound or vibration is shown. It should be understood that the system described above can be used to detect respiratory disturbances. It should be further understood that the system described above can be used to detect respiratory disturbances with a mandibular displacement device in the oral cavity. At 202, an airflow signal and at least one of an acoustic signal or a vibration signal is received. The airflow, acoustic, and/or vibration signals are associated with the subject's breathing. Optionally, the airflow signal and both the acoustic and vibration signals can be received at step 202. At 204, a plurality of features are extracted from the airflow signal and at least one of the acoustic signal or the vibration signal. For example, at least one feature can be extracted from each of the airflow signal and at least one of the acoustic signal or the vibration signal, respectively. This disclosure contemplates that the extracted features can be the same feature for each of the airflow signal and at least one of the acoustic signal or the vibration signal. Alternatively, the extracted features can be different features for each of the airflow signal and at least one of the acoustic signal or the vibration signal. Then, at 206, based on the extracted features, at least one respiratory disturbance is detected.

Referring now to FIG. 2B, a flow diagram illustrating example operations 220 for detecting respiratory disturbances using at least one of sound or vibration is shown. It should be understood that the system described above can be used to detect respiratory disturbances. It should be further understood that the system described above can be used to detect respiratory disturbances with a mandibular displacement device in the oral cavity. At 222, at least one of an acoustic signal or a vibration signal is received. The acoustic and/or vibration signals are associated with the subject's breathing. Optionally, both the acoustic and vibration signals can be received at step 222. At 224, at least one feature is extracted from at least one of the acoustic signal or the vibration signal. As described above, when a plurality of features are extracted (e.g., at least one feature from each of a plurality of measured signals), the extracted features can be the same or different features for each of the respective signals. Then, at 226, based on the extracted feature, at least one respiratory disturbance is detected.

Figure 2C:
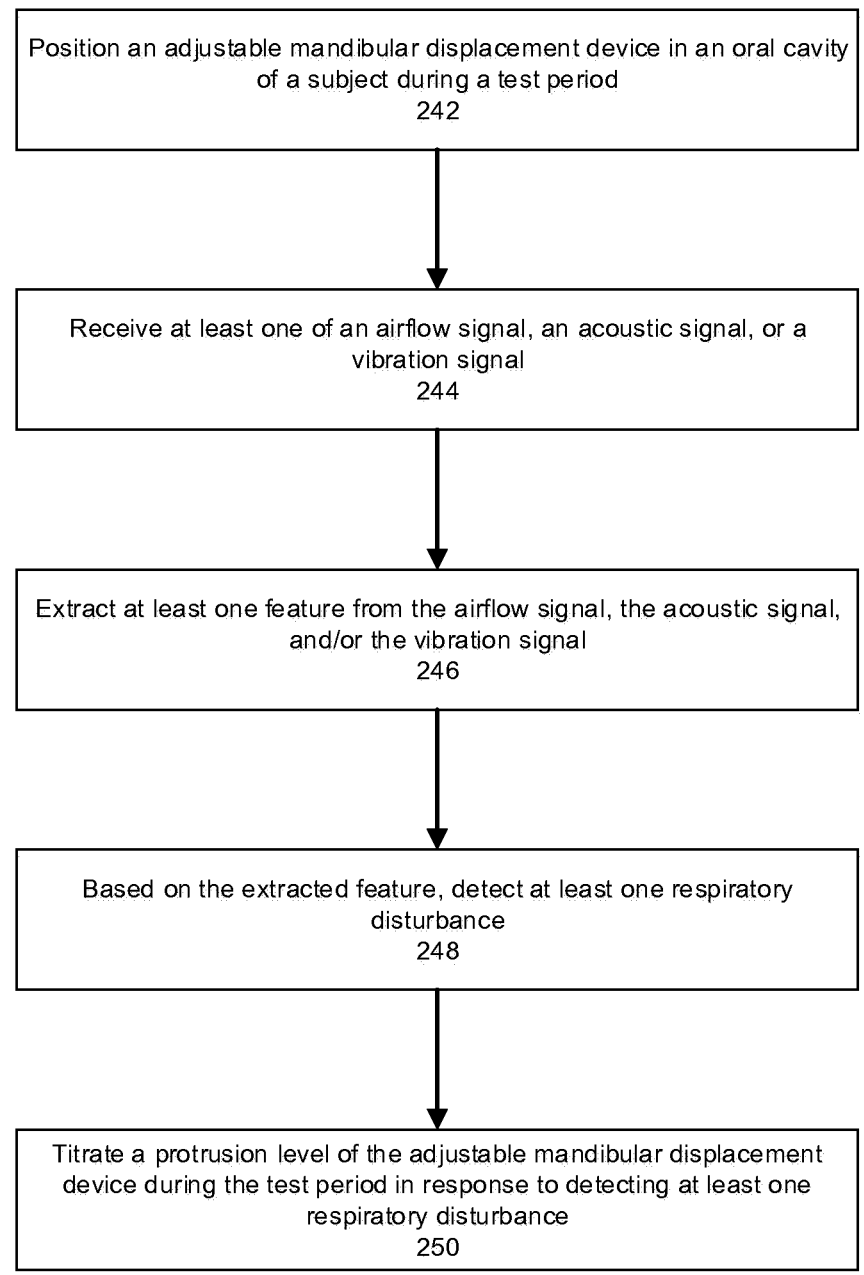
FIG. 2C is a flow diagram illustrating example operations for performing a titration for oral appliance therapy.

Referring now to FIG. 2C, a flow diagram illustrating example operations 240 for performing a titration for oral appliance therapy is shown. It should be understood that the system described above can be used to perform the titration. At 242, an adjustable mandibular displacement device is positioned in an oral cavity of a subject during a test period. At 244, at least one of an airflow signal, an acoustic signal, or a vibration signal is measured. The airflow, acoustic and/or vibration signals are associated with the subject's breathing during the test period. Optionally, both the acoustic and vibration signals are measured at step 244. Optionally, the airflow signal and at least one of the acoustic or vibration signals are measured at step 244. Optionally, the airflow signal and both the acoustic and vibration signals are measured at step 244. At 246, at least one feature is extracted from the airflow signal, the acoustic signal, and/or the vibration signal. As described above, when a plurality of features are extracted (e.g., at least one feature from each of a plurality of measured signals), the extracted features can be the same or different features for each of the respective signals. At 248, based on the extracted features, at least one respiratory disturbance is detected. Then, at 250, a protrusion level of the adjustable mandibular displacement device is titrated during the test period in response to detecting at least one respiratory disturbance.

Titration for oral appliance therapy is described in WO2014-159236, entitled "SYSTEMS AND METHODS FOR PROVIDING AN AUTOMATED TITRATION FOR ORAL APPLIANCE THERAPY", which is incorporated herein by reference in its entirety. Optionally, the method for titrating described with reference to FIG. 2C can include automatically positioning an adjustable mandibular displacement device based on the extracted features or the detected respiratory disturbances. Additionally, the adjustable mandibular displacement device can apply a predefined intervention (e.g., mandibular protrusion by the adjustable mandibular displacement device) based on a change in the level of detected respiratory disturbances. Alternatively, the method for titrating can optionally include remotely positioning the mandibular displacement device in response to the detected disturbances, or evidence of the detected disturbances as might be ascertained by an operator. U.S. Pat. No. 5,826,579 describes an example remote-controlled mandibular displacement device that can optionally be used when performing the titration. Optionally, the method for titrating can include manually repositioning a mandibular displacement device that is an adjustable oral appliance (e.g., screw adjustment on the device) or alternatively, providing a new oral appliance that is fixed at a different protrusion level. This disclosure contemplates that any known oral appliance (or dental appliance) can be used when performing the titration. For example, example oral appliances include SOMNODENT of SOMNOMED LTD. of SYDNEY, AUSTRALIA and NARVAL CC of RESMED of SAN DIEGO, Calif. Additionally, WO2013-102095, entitled "Oral appliances and methods of use" describes example oral appliances.

With regard to FIGS. 2A-2C, the respiratory disturbance can be flow limited breath or IFL. Optionally, the respiratory disturbance can be detected in real time while the subject is sleeping. Alternatively, the respiratory disturbance can be detected offline. Alternatively or additionally, with regard to FIGS. 2A and 2B, the example operations can optionally include diagnosing the subject with HUAR, or assessing treatment with an oral appliance, based on the detection of the at least one respiratory disturbance.

With regard to FIGS. 2A-2C, the example operations can optionally include steps for preprocessing the measured signals (e.g., the airflow, acoustic, and/or vibration signals, as well as a supra-glottic pressure signal). For example, the example operations can optionally include filtering the airflow signal, the acoustic signal, and/or the vibration signal. The filter can optionally be a smoothing, low-pass, band-pass, or high-pass filter. This disclosure contemplates using analog and/or digital filtering techniques. For example, the measured signals can optionally be filtered using an analog filter before analog-to-digital conversion ("ADC") and then digital filtering can optionally be performed post-conversion. In an example implementation, the airflow signal can be preprocessed in several ways. First, an exponential smoothing filter (e.g., with a smoothing factor of ½) can be applied to the airflow signal down sampled at 25 Hz to obtain the airflow signal used for identifying an inspiration portion of each breath (described below). Additionally, a low-pass filter ("LPF") (e.g., with a cutoff frequency of 25 Hz) can be applied to the airflow signal to preprocess the airflow signal before extracting shape features (described below). Further, the airflow signal at 350 Hz can be used to calculate the frequency features (described below). Alternatively or additionally, a band-pass filter ("BPF") (e.g., with a passband between 40 Hz and 4,000 Hz) can be applied to the acoustic signal. Helpful data in the acoustic signal has been found to be in this frequency range. Alternatively or additionally, a LPF (e.g., with a cutoff frequency of 1,000 Hz) can be applied to the vibration signal. It should be understood that the specific filtering techniques described above are provided as examples only and that this disclosure contemplates applying other analog or digital filters to the measured signals.

Alternatively or additionally, the measured signals (e.g., the airflow, acoustic, and/or vibration signals, as well as the supra-glottic pressure signal in the case of training a neural network, for example) can optionally be synchronized before further processing (e.g., before extracting features from the respective signals). For example, even if the measured signals are sampled by different DAQs, the clock of each respective DAQ can be periodically adjusted (e.g., every minute) with the same clock signal such that each sample stamped with an acquisition time. It should be understood that all of the measured signals can then be synchronized according to the acquisition time (i.e., their respective time stamps). It should be understood that the synchronization technique described above is provided only as an example and that other synchronization techniques may be used.

Synchronization between two signals (i.e., the supra-glottic pressure signal and the airflow signal, which are both used to label IFL breaths using the gold standard) is particularly important for training the neural network. In order to show the effectiveness detecting respiratory disturbances using the airflow, acoustic, and/or vibration signals, a test to measure the possible time delay was conducted. The test setup included an orifice connected to a respiratory simulation system by a tube. The orifice was used to simulate the resistance in the upper airway so that limit the airflow into the tube and then keep the pressure longer. To measure pressure inside the tube and orifice airflow, the same system used to measure supra-glottic pressure and airflow was employed, respectively. The test was repeated in a range of respiratory cycles from 2 to 5 seconds. Correlation analysis was performed to check the time delay between these two signals. The result demonstrated that the time delay would be smaller than the sampling rate or $1/25^{th}$ of a second.

As described above with regard to FIGS. 2A-2C, the example operations include steps for extracting features from the measured signals (e.g., the airflow, acoustic, and/or vibration signals). The features can optionally be extracted from the airflow signal, the acoustic signal, and/or the vibration signal in a time or frequency domain. In other words, shape, time, and/or frequency analyses can be performed on the measured signals. For example, the extracted features can include at least one of a shape, magnitude, distribution, duration, or energy of the airflow signal, the acoustic signal, and/or the vibration signal. Alternatively or additionally, the example operations can optionally include a step for normalizing the airflow signal, the acoustic signal, and/or the vibration signal.

The features can optionally be extracted from respective portions of the airflow signal, the acoustic signal, and/or the vibration signal corresponding to a portion of an inspiration portion of a breath. In other words, at least a portion of the signal(s) associated with inspiration become the focus of the extraction analyses. This disclosure contemplates that the features can be extracted from the entire inspiration portion of a breath. Alternatively or additionally, this disclosure contemplates that features can be extracted from a portion of the inspiration portion of a breath (e.g., one-third of a shape feature or one-tenth of the short time Fourier transform). Thus, the inspiration portion of the breath can be identified in the airflow signal, the acoustic signal, and/or the vibration signal, and the features can be extracted from the respective inspiration portion of the signal(s). For example, for each breath, one or more features can be extracted from each respective signal using shape, time, and/or frequency analyses. The extracted feature(s) are used to detect respiratory disturbances (e.g., IFL) in a non-invasive manner (i.e., the supra-glottic pressure signal, which is used in the gold standard, is not used to detect/identify respiratory disturbances).

Optionally, the extracted features can include a correlation between respective portions of at least two of the airflow, acoustic, and vibration signals. For example, the extracted features can be a correlation (e.g., a cross correlation) between the airflow, acoustic, and vibration signals. It should be understood that the subject's snoring, for example, can cause similar fluctuations in a plurality of signals (e.g., the airflow, acoustic, and vibration signal). Accordingly, a correlation between two signals can provide information used to detect the respiratory disturbances. Alternatively or additionally, the extracted features can include a correlation between respective extracted features of at least two of the airflow, acoustic, and vibration signals. Similar to the correlation between two signals, performing a correlation after performing the shape, time, and/or frequency analysis on the signals can yield information used to detect respiratory disturbances.

Optionally, the extracted features can include a sound formant. Alternatively or additionally, the extracted features can optionally include a feature related to a power spectral density ("PSD") of the airflow signal, the acoustic signal, or the vibration signal. Alternatively or additionally, the extracted features can optionally include a feature related to a short time frequency analysis of the airflow signal, the acoustic signal, or the vibration signal. Alternatively or additionally, the extracted features can optionally include a correlation between at least two of the airflow signal, the acoustic signal, and the vibration signal. Alternatively or additionally, the extracted features can optionally include a correlation between time or frequency analyses of at least two of the airflow signal, the acoustic signal, and the vibration signal.

In an example implementation, one or more of the following features can be extracted from an inspiration portion of the airflow signal:

a) a plurality of values of (e.g., 20 points) fitted to the profile of the airflow signal filleted at 25 Hz, and normalized in both magnitude and time;

b) a plurality of calculated values (e.g., 8 values) from the profile of airflow signal filleted at 25 Hz (e.g., skewness (profile and distribution), kurtosis (profile and distribution), ratio of the peak value of the second one-third period over the peak value of the first one-third period, ratio of the peak value of the third one-third period over the peak value of the first one-third period, the density of samples having an amplitude greater than 90% of the peak value, the density of samples having an amplitude greater than 80% of the peak value);

c) a plurality of non-invasive features described in Table II of Morgenstern et al., "Assessment of Changes in Upper Airway Obstruction by Automatic Identification of Inspiratory Flow Limitation During Sleep," IEEE Transactions on Biomedical Eng., Vol. 56, No. 8, pp. 2006-2015 (August 2009) (hereinafter "the Morgenstern Paper"), which is shown in FIG. 4; and d) a plurality of values from the Fourier transform of the airflow signal, integrated over a predetermined frequency span, and normalized (described below).

As described in d) above, the extracted features can include a plurality of values from the Fourier transform of the airflow signal. Each respective value can be a total energy of the airflow signal over a predetermined frequency span. The predetermined frequency span can optionally be between 30 and 50 Hz, e.g., 40 Hz. For example, when the predetermined frequency span is 40 Hz, the airflow signal can be integrated over 40 Hz increments (e.g., 0-39 Hz, 40-79 Hz, 80-119 Hz, etc.). The integration yields the total energy over each predetermined frequency span. Accordingly, for a 350 Hz airflow signal (considering the Nyquist rule), this calculation yields approximately 4 values (up to 160 Hz).

In an example implementation, one or more of the following features can be extracted from an inspiration portion of the vibration signal:

a) a plurality of values from the Fourier transform of the vibration signal, integrated over a predetermined frequency span, and normalized (described below).

As described in a) above, the extracted features can include a plurality of values from the Fourier transform of the vibration signal. Each respective value can be a total energy of the vibration signal over a predetermined frequency span. The predetermined frequency span can optionally be between 30 and 50 Hz, e.g., 40 Hz. For example, when the predetermined frequency span is 40 Hz, the vibration signal can be integrated over 40 Hz increments (e.g., 0-39 Hz, 40-79 Hz, 80-119 Hz, etc.). The integration yields the total energy over each predetermined frequency span. Accordingly, for a 2,560 Hz vibration signal (considering the Nyquist rule), this calculation yields approximately 30 values.

In an example implementation, one or more of the following features can be extracted from an inspiration portion of the acoustic signal:

a) a plurality of values from the Fourier transform of the acoustic signal, integrated over a predetermined frequency span, and normalized (described below);

b) sound intensity, e.g., the maximum energy of each breath; and c) a plurality of values (e.g., 10 values) of the frequency and magnitude of 5 first formants.

As described in a) above, the extracted features can include a plurality of values from the Fourier transform of the acoustic signal. Each respective value can be a total energy of the acoustic signal over a predetermined frequency span. The predetermined frequency span can optionally be between 30 and 50 Hz, e.g., 40 Hz. For example, when the predetermined frequency span is 40 Hz, the acoustic signal can be integrated over 40 Hz increments (e.g., 0-39 Hz, 40-79 Hz, 80-119 Hz, etc.). The integration yields the total energy over each predetermined frequency span. Accordingly, for a 22,050 Hz acoustic signal (considering the Nyquist rule), this calculation yields approximately 100 values (up to 4,000 Hz due to application of a LPF applied).

It should be understood that the extracted features for the airflow, acoustic, and vibration signals described above are provided as examples only. Thus, this disclosure contemplates extracting one or more features from the airflow, acoustic, and vibration signals other than those explicitly described above. For example, the extracted features can include any shape, magnitude, distribution, duration, and/or energy feature of the airflow signal, the acoustic signal, and/or the vibration signal As described above, the respiratory disturbance can be detected using machine learning module. The machine learning module can be a classifier, a pattern recognition module. Examples of machine learning techniques are neural network, support vector machine, decision tree, AdaBoost, The machine learning module can be trained to classify the subject's breath(s) as respiratory disturbances. For example, the extracted features can be input in the machine learning module, and an output value of the machine learning module can indicate occurrence of the at least one respiratory disturbance. Optionally, the machine learning module can be a neural network. For example, the neural network can be a feedforward multilayer perceptron neural network. The neural network can have one hidden layer of ten nodes with sigmoid activation functions and a one-node output with a linear function. It should be understood that a feedforward multilayer perceptron neural network having have one hidden layer of ten nodes and a one-node output is provided only as an example and that other neural network configurations can be used.

Optionally, the machine learning module can output a numeric signal (e.g., a binary or non-binary, real number output) or non-numeric signal (e.g., IFL or non-IFL). The machine learning module can optionally output a binary signal (e.g., 0 or 1). When the output value of the machine learning module is a first value (e.g., 0 or 1), the machine learning module indicates that the respiratory disturbance occurred (e.g., the subject's breath is classified as IFL). When the output value of the machine learning module is a second value (e.g., the other of 1 or 0), the machine learning module indicates that the respiratory disturbance did not occur (e.g., the subject's breath is not classified as IFL).

Alternatively, the machine learning module can optionally output a non-binary signal. When the output value of the machine learning module is within a first range of values (e.g., a positive value), the machine learning module indicates that the respiratory disturbance occurred (e.g., the subject's breath is classified as IFL). When the output value of the machine learning module is within a second range of values (e.g., a negative value), the machine learning module indicates that the respiratory disturbance did not occur (e.g., the subject's breath is not classified as IFL). Optionally, there can be a range of values (i.e., an indeterminate range or uncertainty category) between the first and second ranges of values where the machine learning module indicates neither occurrence nor non-occurrence of the at least one respiratory disturbance.

Example Computing Device

When the logical operations described herein are implemented in software, the process may execute on any type of computing architecture or platform. For example, referring to FIG. 3, an example computing device upon which embodiments of the invention may be implemented is illustrated. For example, the processor, memory, the classifier, the pattern recognition system, the machine learning system, and/or the neural network described above can be implemented using one or more computing devices such as computing device 300. The computing device 300 may include a bus or other communication mechanism for communicating information among various components of the computing device 300. In its most basic configuration, computing device 300 typically includes at least one processing unit 306 and system memory 304. Depending on the exact configuration and type of computing device, system memory 304 may be volatile (such as random access memory (RAM)), non-volatile (such as read-only memory (ROM), flash memory, etc.), or some combination of the two. This most basic configuration is illustrated in FIG. 3 by dashed line 302. The processing unit 306 may be a standard programmable processor that performs arithmetic and logic operations necessary for operation of the computing device 300.

Computing device 300 may have additional features/functionality. For example, computing device 300 may include additional storage such as removable storage 308 and non-removable storage 310 including, but not limited to, magnetic or optical disks or tapes. Computing device 300 may also contain network connection(s) 316 that allow the device to communicate with other devices. Computing device 300 may also have input device(s) 314 such as a keyboard, mouse, touch screen, etc. Output device(s) 312 such as a display, speakers, printer, etc. may also be included. The additional devices may be connected to the bus in order to facilitate communication of data among the components of the computing device 300. All these devices are well known in the art and need not be discussed at length here.

The processing unit 306 may be configured to execute program code encoded in tangible, computer-readable media. Computer-readable media refers to any media that is capable of providing data that causes the computing device 300 (i.e., a machine) to operate in a particular fashion. Various computer-readable media may be utilized to provide instructions to the processing unit 306 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 306 may execute program code stored in the system memory 304. For example, the bus may carry data to the system memory 304, from which the processing unit 306 receives and executes instructions. The data received by the system memory 304 may optionally be stored on the removable storage 308 or the non-removable storage 310 before or after execution by the processing unit 306.

Computing device 300 typically includes a variety of computer-readable media. Computer-readable media can be any available media that can be accessed by device 300 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 304, removable storage 308, and non-removable storage 310 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 300. Any such computer storage media may be part of computing device 300.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

EXAMPLES

Methods

Each participant or subject (n=10) underwent a full-night polysomnogram that included measurement of supra-glottic pressure, nasal airflow (e.g., the airflow signal described above), snoring sound (e.g., the acoustic signal described above), and dental vibration (e.g., the vibration signal described above). The participant slept with temporary dental trays in the mouth attached to a motorized mandibular positioner (e.g., the mandibular displacement device 10 of FIGS. 1A-1C).

Supra-glottic pressure was measured by a pressure transducer connected to a saline-filled naso-pharyngeal catheter. For example, a reusable pressure transducer, MX960, was employed to measure the supra-glottic pressure. The transducer was connected to the subject's supra-glottic cavity via a tube catheter (e.g., 6FRx15", RADIOPAQUE FEEDING TUBE from MED-RX of OAKVILLE, ONTARIO, CANADA) filled with saline and exposed to a slight head pressure ensuring a slow and constant drip. The catheter was positioned 2 cm below the base of the subject's tongue and adjusted as needed to ensure that its open end is located below the choke point. The transducer's output voltage was filtered and amplified before it was connected to a DAQ from KEITHLEY INSTRUMENTS, INC. of SOLON, Ohio. The DAQ sampled the analog supra-glottic pressure signal at the rate of 25 Hz and digitized the data. Before each study, a manual calibration test was performed. The calibration test was performed by manually applying pressure with a pressure manometer from −40 to 40 cmH$_2$O and recording the output voltage at each pressure. A linear relation is considered for the pressure-voltage relation. No digital filter was applied on the supra-glottic pressure signal because it was smooth enough from the analog filtering. The baseline for the supra-glottic pressure drifted during the night in response to the subject's movement. Accordingly, the supra-glottic pressure at the start of inspiration was considered as the baseline of supra-glottic pressure in each inspiration. Airflow (e.g., the airflow signal) was measured from the air pressure in each of the subject's nostrils, for example, as described above with regard to FIGS. 1A-1C. Snoring sound (e.g., the acoustic signal) and vibration (e.g., the vibration signal) were recorded by a microphone and accelerometer fixed in relation to the mandibular positioner, respectively, for example, as described above with regard to FIGS. 1A-1C. Thus, after subtracting the baseline from each of the supra-glottic pressure and airflow signals, the supra-glottic pressure and airflow signals both show zero at the start of inspiration.

Figure 6:
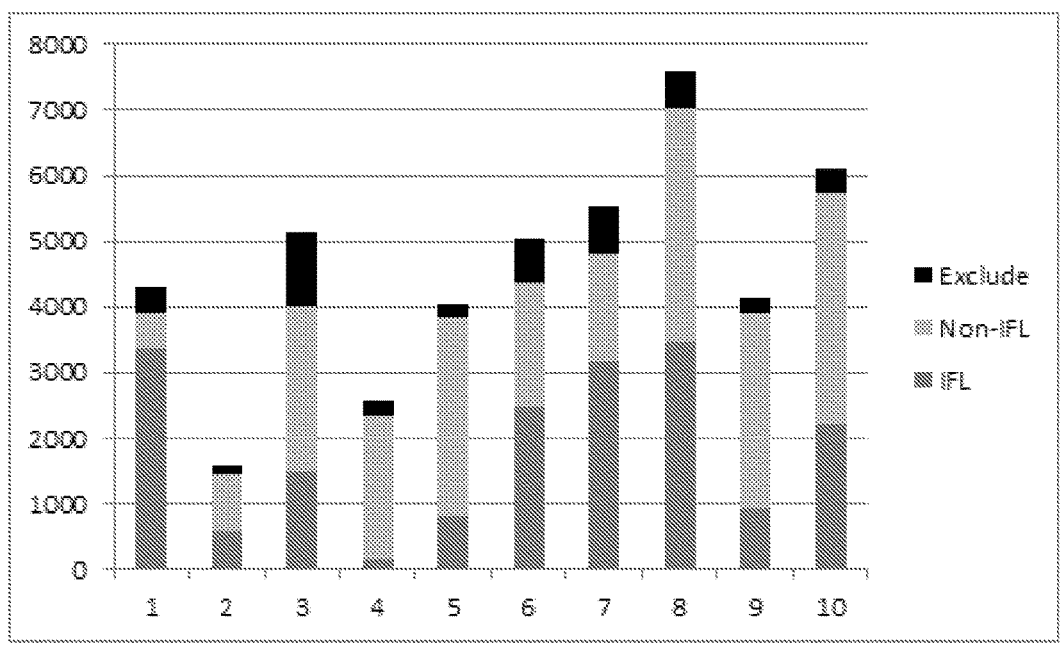
FIG. 6 is a graph illustrating the distribution of IFL breaths for 10 subjects classified using an auto-labeller technique.

An auto-labeller ("AL") was employed using the supra-glottic pressure and airflow signals to designate each breath as IFL or non-IFL. The AL used classical criteria or the gold standard to label breaths as IFL. Thus, a breath was classified as IFL when there was no increase in airflow associated with a 1 cmH$_2$O drop in supra-glottic pressure. In other words, the AL found IFL when a window of 1 cmH$_2$O drop in supra-glottic pressure could be found without associated increase in airflow. Referring now to FIG. 6, a graph illustrating the distribution of IFL breaths using the AL is shown. After excluding portions with unwanted action such as apnea and sighs (i.e., "Exclude" in FIG. 6), 41,363 individual breaths were detected from the 10 patients. Of the individual breaths, 18,656 IFL breaths and 22,707 non-IFL breaths were labeled by the AL.

A neural network ("NN") was trained to identify IFL breaths using features of the non-invasive signals (e.g., the airflow, acoustic, and vibration signals described above) as inputs to the NN. In particular, as described above, one or more shape, frequency, and/or time features were extracted from one or more of the non-invasive signals. The features were extracted from the inspiration portion of each breath. A feedforward multilayer perceptron neural network with one hidden layer of 10 nodes and a one node output was employed. The NN was trained using the extracted features and the labels from the AL (e.g., employing the gold standard): IFL breaths were labelled as +1 and non-IFL ones as −1. Back-propagation algorithm was used to train NN. The NN was trained on a random selection of 80% of the breaths and evaluated on the other 20%. A five-fold cross validation was used to prevent over-fitting.

Results

Figure 7:
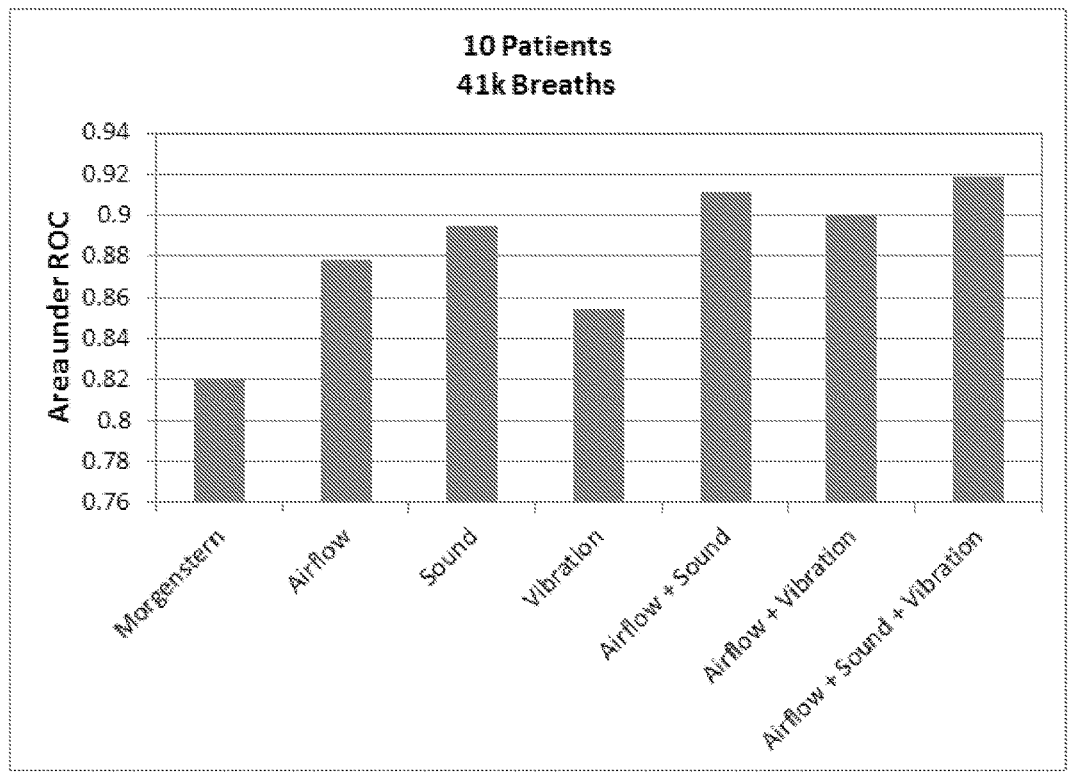
FIG. 7 is a graph illustrating the agreement between the auto-labeller and neural network techniques for various input selections.

The trained NN can receive similar features extracted from the non-invasive signals and calculate an output value that predicts/detects/identifies respiratory disturbance such as IFL. Additionally, the area under the receiver operating characteristic ("ROC") curve can be taken as a measure of agreement between the NN and AL. Referring now to FIG. 7, a graph illustrating the AL/NN agreement for each of six input selections (i.e., airflow signal only; acoustic signal (or sound) only; vibration signal (or vibration) only; airflow and sound signals; airflow and vibration signals; and airflow, sound, and vibration signals), as well as the airflow-related parameters described by the Morgenstern Paper. The Morgenstern Paper parameters yielded an ROC area of 0.81, substantially less than the value of 0.91 reported previously. Airflow, sound, and vibration each individually yielded ROC areas of 0.85-0.89, and the combination of airflow with sound and/or vibration increased the values to 0.90-0.92, with the highest resulting from all three. The ROC area using Morgenstern Paper parameters was less than previously reported, which is the result of the dental appliance. Accordingly, non-invasive signals such as airflow, sound, and/or vibration can be used to identify IFL with sufficient accuracy for clinical purposes.

Figure 8:
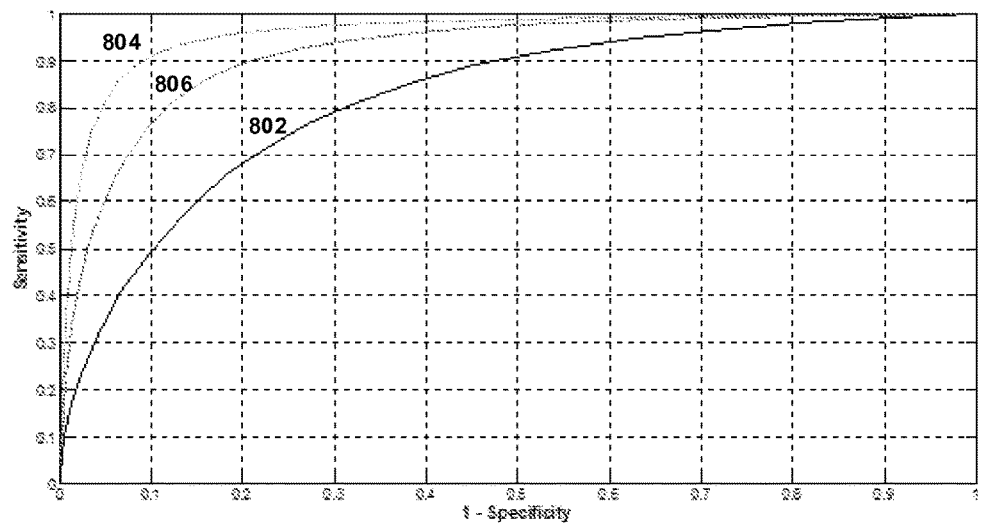
FIG. 8 is a graph illustrating ROC curves for different combinations of input features.

Referring now to FIG. 8, a graph illustrating ROC curves for different combinations of input features is shown. Curve 802 illustrates the ROC curve using the Morgenstern Paper parameters. Curve 804 is the ROC curve using the airflow only signal. Curve 806 is the ROC curve using airflow, sound, and vibration signals.

Figure 9:
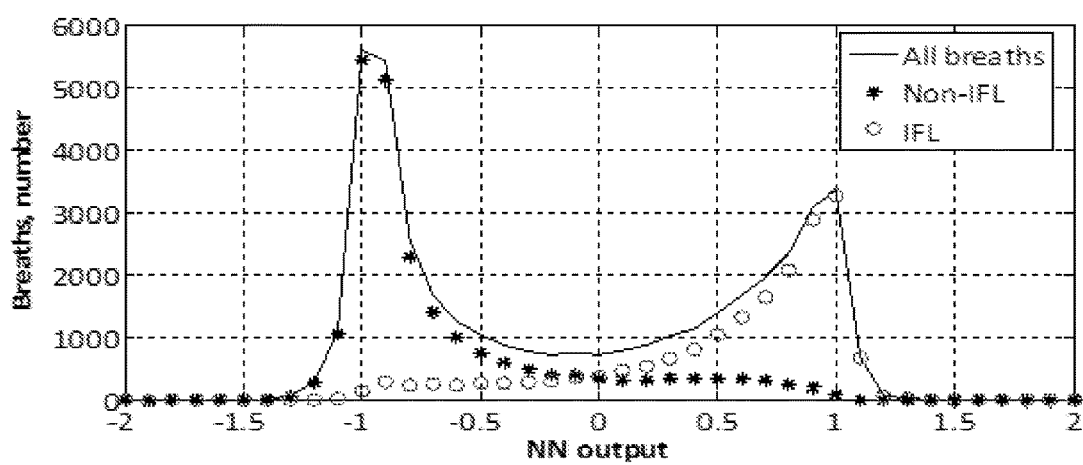
FIG. 9 is a graph illustrating the bimodality distribution of inspirations in relation to neural network output.
Figure 10:
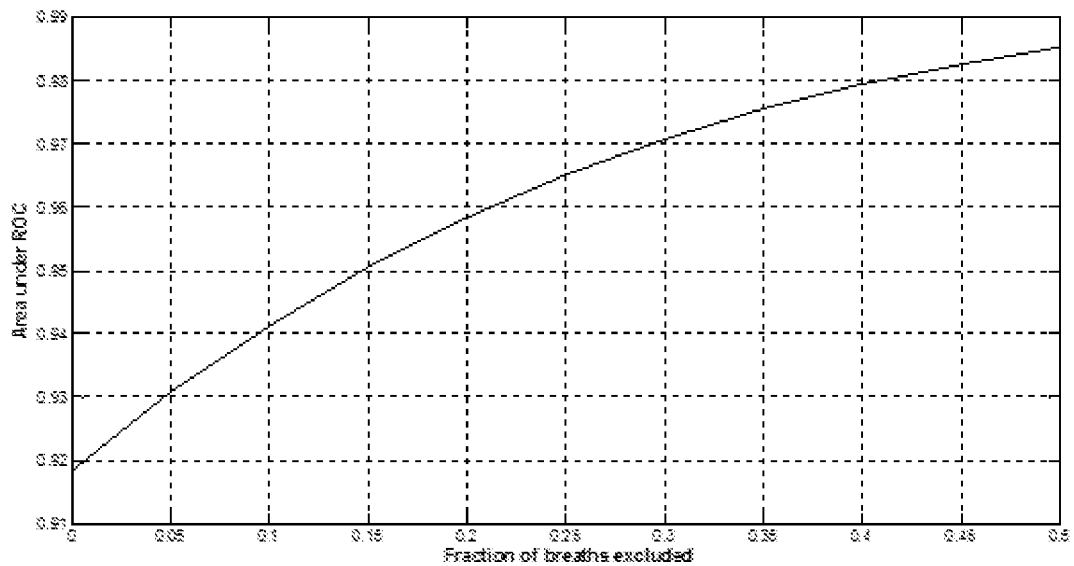
FIG. 10 is a graph illustrating how the neural network prediction accuracy can be increased by excluding a fraction of breaths.

The output value of the neural network can optionally be binary, e.g., 1 identifying an IFL breath and −1 identifying a non-IFL breath (or vice versa). Alternatively, the output value can optionally be non-binary, e.g., any real number. One example way to interpret the non-binary output value is that the positive output values identify IFL breaths and negative output values identify non-IFL breaths (or vice versa). As shown in the output distribution of FIG. 9, the certainty of the classification increases as the NN output differs from zero in both positive and negative directions. Accordingly, as shown in FIG. 10, the prediction accuracy of the NN can be increased by defining a third category (e.g., an uncertain category) and excluding a subset of breaths from classification. For example, the uncertainty category can optionally include the breaths with NN output ranging from [−0.3, 0.3], and these breaths can be excluded, which increases the certainty of the NN prediction.

Figure 11:
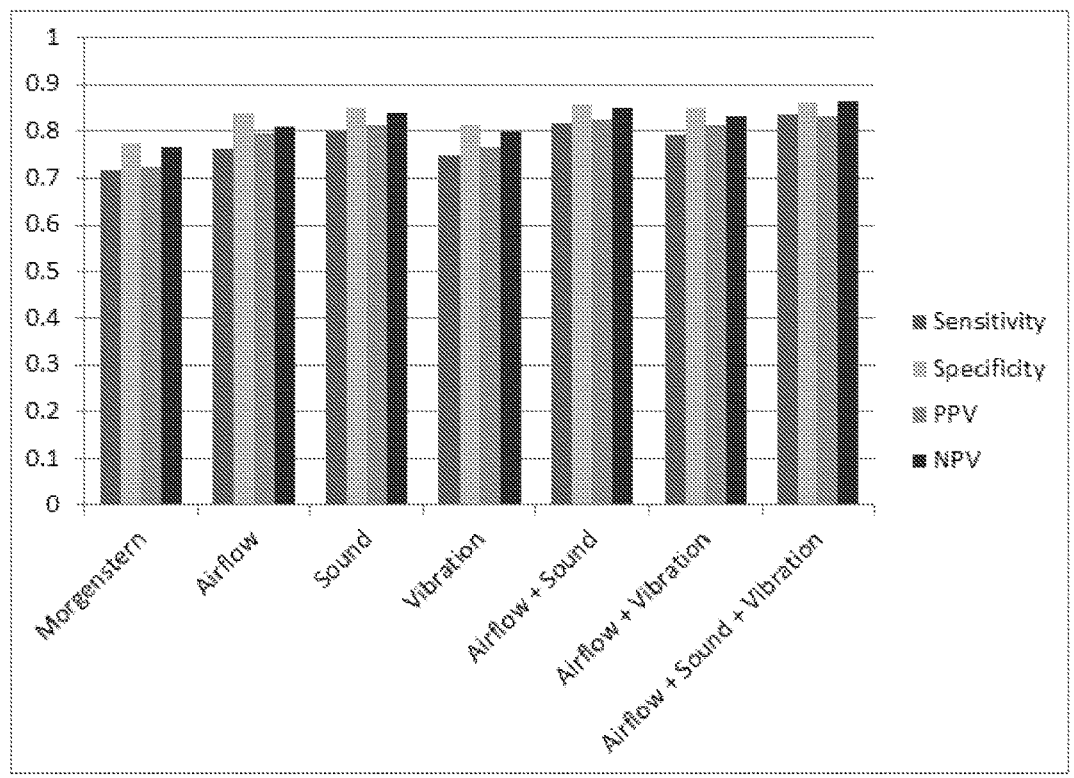
FIG. 11 a graph illustrating the sensitivity, specificity, positive predictive value ("PPV"), and negative predictive value ("NPV") for various input selections.

Referring now to FIG. 11, a graph illustrating the sensitivity, specificity, positive predictive value ("PPV"), and negative predictive value ("NPV) for each of six input selections (i.e., airflow signal only; acoustic signal (or sound) only; vibration signal (or vibration) only; airflow and sound signals; airflow and vibration signals; and airflow, sound, and vibration signals), as well as the airflow-related parameters described by the Morgenstern Paper.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for detecting respiratory disturbances experienced by a subject, comprising:
    positioning a mandibular displacement device in the subject's oral cavity;
    receiving, using a computing device, at least one signal associated with the subject's breathing, wherein the at least one signal is an airflow signal, an acoustic signal, or a vibration signal;
    extracting, using the computing device, a plurality of features from the at least one signal;
    calculating, using the computing device, a correlation between the extracted features; and detecting, using the computing device, at least one respiratory disturbance based on the correlation between the extracted features.

2. The method of claim 1, wherein detecting, based on the correlation between the extracted features, at least one respiratory disturbance further comprises inputting the correlation between the extracted features into a machine learning module that is executed by the computing device, wherein an output value of the machine learning module indicates occurrence of the at least one respiratory disturbance.

3. The method of claim 2, wherein the at least one respiratory disturbance occurred when the output value is a first value.

4. The method of claim 3, wherein the at least one respiratory disturbance did not occur when the output value is a second value.

5. The method of claim 2, wherein the machine learning module is a neural network.

6. The method of claim 1, wherein the extracted features include a feature extracted from a portion of the airflow signal corresponding to at least a portion of an inspiration portion of a breath.

7. The method of claim 1, wherein the extracted features include a feature extracted from the airflow signal in a time or frequency domain.

8. The method of claim 7, wherein the extracted features include at least one of a shape, magnitude, distribution, duration, or energy of the airflow signal.

9. The method of claim 8, wherein the extracted features include: a feature related to a power spectral density of the airflow signal; or a feature related to a short time frequency analysis of the airflow signal.

10. The method of claim 8, wherein the extracted features include a plurality of values of the airflow signal in the frequency domain, wherein each respective value comprises a total energy of the airflow signal over a predetermined frequency span.

11. The method of claim 10, wherein the predetermined frequency span is approximately 30-50 Hz.

12. The method of claim 11, wherein the predetermined frequency span is approximately 40 Hz.

13. The method of claim 1, further comprising normalizing the airflow signal.

14. The method of claim 1, further comprising filtering the airflow signal.

15. The method of claim 1, wherein the airflow signal is based on air pressure measured separately in each of the subject's nares.

16. The method of claim 1, wherein at least two signals associated with the subject's breathing are received using the computing device, and wherein the extracted features are extracted from the airflow signal and at least one of the acoustic signal or the vibration signal.

17. The method of claim 16, wherein the extracted features are extracted from the airflow signal, the acoustic signal, and the vibration signal.

18. The method of claim 16, wherein the extracted features are extracted from respective portions of the airflow signal and the at least one of the acoustic signal or the vibration signal corresponding to at least a portion of an inspiration portion of a breath.

19. The method of claim 16, wherein the extracted features are extracted from the airflow signal and the at least one of the acoustic signal or the vibration signal in a time or frequency domain.

20. The method of claim 19, wherein the extracted features include at least one of a shape, magnitude, distribution, duration, or energy of the airflow signal and the at least one of the acoustic signal or the vibration signal.

21. The method of claim 20, wherein the extracted features include: a sound formant; a feature related to a power spectral density of the airflow signal, the acoustic signal, or the vibration signal; or a feature related to a short time frequency analysis of the airflow signal, the acoustic signal, or the vibration signal.

22. The method of claim 16, wherein the at least one of the acoustic signal or the vibration signal is measured using a sensor arranged in the subject's oral cavity.

23. The method of claim 16, wherein the at least one of the acoustic signal or the vibration signal is measured using a sensor mounted on a mandibular displacement device.

24. The method of claim 16, wherein the at least one of the acoustic signal or the vibration signal is measured using a sensor.

25. The method of claim 24, wherein the sensor is a microphone, accelerometer, or strain gauge configured to measure the acoustic signal or an accelerometer or strain gauge configured to measure the vibration signal.

26. The method of claim 25, wherein the microphone, accelerometer, or strain gauge configured to measure the acoustic signal is attached to a housing or dental tray of the mandibular displacement device.

27. The method of claim 25, wherein the accelerometer or strain gauge configured to measure the vibration signal is attached to a housing, dental tray or bracket of the mandibular displacement device.

28. The method of claim 1, wherein the at least one respiratory disturbance is flow limited breath or inspiratory flow limitation (IFL).

29. The method of claim 1, further comprising diagnosing or assessing the subject with high upper airway resistance (HUAR) based on the detection of the at least one respiratory disturbance.

30. The method of claim 1, wherein the at least one respiratory disturbance is detected in real time while the subject is sleeping.

31. The method of claim 1, wherein the correlation between the extracted features is a cross-correlation between the extracted features.

32. The method of claim 2, wherein the at least one respiratory disturbance is inspiratory flow limitation (IFL).

33. The method of claim 1, wherein the plurality of features from the at least one signal is extracted from the at least one signal in the frequency domain.

34. The method of claim 1, further comprising measuring, using at least one sensor arranged in proximity to the subject's oral or nasal cavity, the at least one signal associated with the subject's breathing.

35. A system for detecting respiratory disturbances experienced by a subject, the system comprising:
  a mandibular displacement device;
  at least one sensor for measuring at least one of an airflow signal, an acoustic signal, or a vibration signal associated with the subject's breathing, wherein the at least one sensor is arranged in proximity to the subject's oral or nasal cavity;
  a processor; and
  a memory operatively coupled to the processor, the memory having computer-executable instructions stored thereon that, when executed by the processor, cause the processor to:

receive the at least one signal associated with the subject's breathing;

extract a plurality of features from the at least one signal;

calculate a correlation between the extracted features; and detect, based on the correlation between the extracted features, at least one respiratory disturbance.

36. The system of claim 35, wherein detecting, based on the correlation between the extracted features, at least one respiratory disturbance further comprises inputting the correlation between the extracted features into a machine learning module that is executed by the computing device, wherein an output value of the machine learning module indicates occurrence of the at least one respiratory disturbance.

37. The system of claim 35, wherein the at least one sensor is mounted on the mandibular displacement device.

38. The system of claim 35, wherein at least two signals associated with the subject's breathing are received, and wherein the extracted features are extracted from the airflow signal and at least one of the acoustic signal or the vibration signal.

39. The system of claim 38, wherein the at least one sensor comprises an acoustic or vibration sensor arranged in the subject's oral cavity, wherein the at least one of the acoustic signal or the vibration signal is measured using the acoustic or vibration sensor.

40. The system of claim 38, wherein the at least one sensor comprises an acoustic or vibration sensor, wherein the at least one of the acoustic signal or the vibration signal is measured using the acoustic or vibration sensor.

41. The system of claim 40, wherein the acoustic or vibration sensor includes a microphone, accelerometer, or strain gauge configured to measure the acoustic signal or an accelerometer or strain gauge configured to measure the vibration signal.

42. The system of claim 41, wherein the microphone, accelerometer, or strain gauge configured to measure the acoustic signal is attached to a housing or dental tray of the mandibular displacement device.

43. The system of claim 41, wherein the accelerometer or strain gauge configured to measure the vibration signal is attached to a housing, dental tray or bracket of the mandibular displacement device.

44. The method of claim 34, wherein the at least one sensor is mounted on the mandibular displacement device.

* * * * *